(12) United States Patent
Kanamori et al.

(10) Patent No.: US 9,644,221 B2
(45) Date of Patent: *May 9, 2017

(54) METHOD OF PRODUCING CHEMICAL BY CONTINUOUS FERMENTATION AND CONTINUOUS FERMENTATION APPARATUS

(71) Applicant: Toray Industries, Inc., Tokyo (JP)

(72) Inventors: Satoko Kanamori, Otsu (JP); Hideki Sawai, Tokai (JP); Norihiro Takeuchi, Otsu (JP)

(73) Assignee: Toray Industries, Inc. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/388,306

(22) PCT Filed: Mar. 27, 2013

(86) PCT No.: PCT/JP2013/059086
§ 371 (c)(1),
(2) Date: Sep. 26, 2014

(87) PCT Pub. No.: WO2013/146920
PCT Pub. Date: Oct. 3, 2013

(65) Prior Publication Data
US 2015/0056665 A1 Feb. 26, 2015

(30) Foreign Application Priority Data
Mar. 30, 2012 (JP) ................ 2012-082599

(51) Int. Cl.
| | | |
|---|---|---|
| *C12P 1/00* | (2006.01) | |
| *C12P 13/24* | (2006.01) | |
| *C12P 7/56* | (2006.01) | |
| *C12P 13/04* | (2006.01) | |
| *C12M 1/00* | (2006.01) | |
| *C12M 1/26* | (2006.01) | |
| *C12M 1/34* | (2006.01) | |
| *C12P 13/00* | (2006.01) | |
| *C12P 13/06* | (2006.01) | |
| *C12P 13/08* | (2006.01) | |
| *C12P 13/10* | (2006.01) | |
| *C12P 13/12* | (2006.01) | |
| *C12P 13/14* | (2006.01) | |
| *C12P 13/20* | (2006.01) | |
| *C12P 13/22* | (2006.01) | |

(52) U.S. Cl.
CPC .......... *C12P 13/24* (2013.01); *C12M 29/04* (2013.01); *C12M 33/14* (2013.01); *C12M 41/34* (2013.01); *C12P 7/56* (2013.01); *C12P 13/001* (2013.01); *C12P 13/04* (2013.01); *C12P 13/06* (2013.01); *C12P 13/08* (2013.01); *C12P 13/10* (2013.01); *C12P 13/12* (2013.01); *C12P 13/14* (2013.01); *C12P 13/20* (2013.01); *C12P 13/222* (2013.01); *C12P 13/225* (2013.01); *C12P 13/227* (2013.01)

(58) Field of Classification Search
CPC ............ C12P 1/00; C12P 13/00; C12P 13/04
See application file for complete search history.

(56) References Cited

U.S. PATENT DOCUMENTS

| | | | |
|---|---|---|---|
| 5,124,257 A | 6/1992 | Azizian et al. | |
| 5,503,750 A | 4/1996 | Russo et al. | |
| 2003/0153059 A1* | 8/2003 | Pilkington | C12C 11/07 435/161 |
| 2006/0182667 A1* | 8/2006 | Zech | B01F 13/0255 422/130 |
| 2009/0269812 A1* | 10/2009 | Sawai | C12P 13/04 435/88 |
| 2011/0177551 A1 | 7/2011 | Minitsuka et al. | |

FOREIGN PATENT DOCUMENTS

| | | |
|---|---|---|
| CN | 102311912 | 1/2012 |
| EP | 1 988 170 | 11/2008 |
| JP | 61-254185 A | 11/1986 |
| JP | 63-188384 A | 8/1988 |
| JP | 02-219582 A | 9/1990 |
| JP | 3-500486 | 2/1991 |
| JP | 06-345683 A | 12/1994 |
| JP | 09-075686 A | 3/1997 |
| JP | 3645814 B2 | 2/2005 |
| JP | 2006-281022 A | 10/2006 |
| JP | 2008-161071 A | 7/2008 |
| JP | 2008-212138 A | 9/2008 |
| JP | 2010-029108 A | 2/2010 |
| JP | 2010-036180 A | 2/2010 |
| JP | 4806904 B2 | 8/2011 |
| WO | 00/21890 A1 | 4/2000 |
| WO | 2007/097260 A1 | 8/2007 |
| WO | 2010/038613 A2 | 4/2010 |

OTHER PUBLICATIONS

U.S. Appl. No. 13/992,443; U.S. Appl. No. 13/996,241.*
Supplementary European Search Report dated Oct. 15, 2015 of corresponding European Application No. 13770154.6.
S. Siegell, et al., Automatic Control of Dissolved Oxygen Levels in Fermentations, *Biotechnology and Bioengineering*, Sep. 1962, vol. IV, No. 3, pp. 345-356.

* cited by examiner

*Primary Examiner* — Ruth Davis
(74) *Attorney, Agent, or Firm* — DLA Piper LLP (US)

(57) ABSTRACT

A method of producing a chemical includes culturing cells in a culture solution in a fermentor to ferment a feedstock to produce a chemical; supplying the culture solution containing the chemical produced in the culturing to a plurality of separation membrane units arranged in parallel; filtering the culture solution supplied in the supplying to separate a permeate containing the chemical; refluxing a retentate that is not filtered in the filtering to the fermentor; and supplying a gas containing oxygen to the plurality of separation membrane units while a supply amount is changed to at least two different values to perform scrubbing, wherein the supply amount and supply time of the gas containing oxygen supplied in the culturing and the supplying the gas are set so that a kLa value is within a predetermined range from an optimal kLa value for the cells cultured in the culturing.

16 Claims, 6 Drawing Sheets

METHOD OF PRODUCING CHEMICAL BY CONTINUOUS FERMENTATION AND CONTINUOUS FERMENTATION APPARATUS

TECHNICAL FIELD

This disclosure relates to a method of producing a chemical by continuous fermentation and a continuous fermentation apparatus. In particular, the disclosure relates to a method of producing a chemical by continuous fermentation using a chemical production apparatus provided with a circulation system having a fermentor and a plurality of separation membrane units connected to the fermentor while a gas is supplied to the separation membrane units.

BACKGROUND

A fermentation method that is a method of producing a substance involving culture of a microorganism or cultured cells can be roughly classified into (1) a batch fermentation method and a fed-batch or semi-batch fermentation method, and (2) a continuous fermentation method. The batch fermentation method and the fed-batch or semi-batch fermentation method have such advantages that facilities are simple, culturing is completed in a short time, and the possibility of being contaminated with germs other than cultured bacteria in fermentation of a product by pure culture of bacteria is low. However, the concentration of a product in a culture solution increases with time, and the productivity and yield decrease due to influences such as inhibition by the product and an increase in the osmotic pressure. Therefore, it is difficult to stably maintain high yield and high productivity for a long time.

In contrast, in the continuous fermentation method, high yield and high productivity can be maintained over a longer period by preventing accumulation of a target substance in a fermentor compared to the batch fermentation method and the fed-batch or semi-batch fermentation method. Conventional continuous culturing is a culturing method in which a fresh culture medium is supplied to a fermentor at a constant rate, a culture solution in the same amount as the amount of the culture medium is discharged out of the fermentor to always keep the amount of liquid in the fermentor constant. In batch culture, culturing is completed when the initial substrate concentration is consumed, and in continuous culturing, culturing can be theoretically continued infinitely.

Recently, a continuous culture apparatus using an organic macromolecular separation membrane has been proposed for continuous culture (for example, see International Publication No. 07/097260 and Japanese Laid-open Patent Publication No. 2008-212138).

However, the filtration ability of the separation membrane decreases by an SS (suspended solid) and an adsorbate attached to a filtration face, and a necessary amount of filtrate may not be obtained.

On the other hand, in the field of water treatment, not continuous fermentation, but scrubbing by supply of a gas has been proposed to wash a separation membrane (for example, see Japanese Patent No. 3645814).

However, in the continuous fermentation, the amount of oxygen in a fermentation liquid affects a result of fermentation. Therefore, simple application of a scrubbing method in the water treatment may cause a problem in which a chemical is not obtained at a desired rate.

In such a conventional technique, a scrubbing washing method suitable for continuous fermentation operation using a membrane separation technique has not been studied, and a method of maintaining the filtration properties of a separation membrane by washing a membrane surface and enhancing the productivity of a chemical by fermentation has been required.

It would therefore be helpful to provide a method of producing a chemical by a continuous fermentation method in which a washing effect of a separation membrane by a gas is enhanced by a simple operation procedure while high productivity can be stably maintained for a long time.

SUMMARY

We found that the washing effect of a separation membrane can be held and simultaneously the fermentation performance can be maintained by setting the supply amount of a gas containing oxygen to be supplied to a continuous fermentation apparatus on the basis of an optimal kLa value for cells to be cultured in the device and sequentially supplying the gas to a plurality of separation membrane units in a circulation system while the supply amount of the gas is changed to different amounts.

We thus provide a method of producing a chemical including a chemical production step of culturing cells in a culture solution in a fermentor to ferment a feedstock to produce a chemical; a culture solution supply step of supplying the culture solution containing the chemical produced in the chemical production step to a plurality of separation membrane units arranged in parallel; a filtration step of filtering the culture solution supplied in the culture solution supply step to separate a permeate containing the chemical; a reflux step of refluxing a retentate that is not filtered in the filtration step to the fermentor; and a washing step of supplying a gas containing oxygen to the plurality of separation membrane units while a supply amount is changed to at least two different values to perform scrubbing, wherein the supply amount and supply time of the gas containing oxygen supplied in the chemical production step and the washing step are set so that a kLa value is within a predetermined range from an optimal kLa value for the cells cultured in the chemical production step.

The filtration properties of a separation membrane can be stabilized for a long time and, at the same time, the result of fermentation can be improved. Furthermore, a chemical as a fermentation product can be stably produced at low cost for a long time in various fermentation industries.

Figure 1:
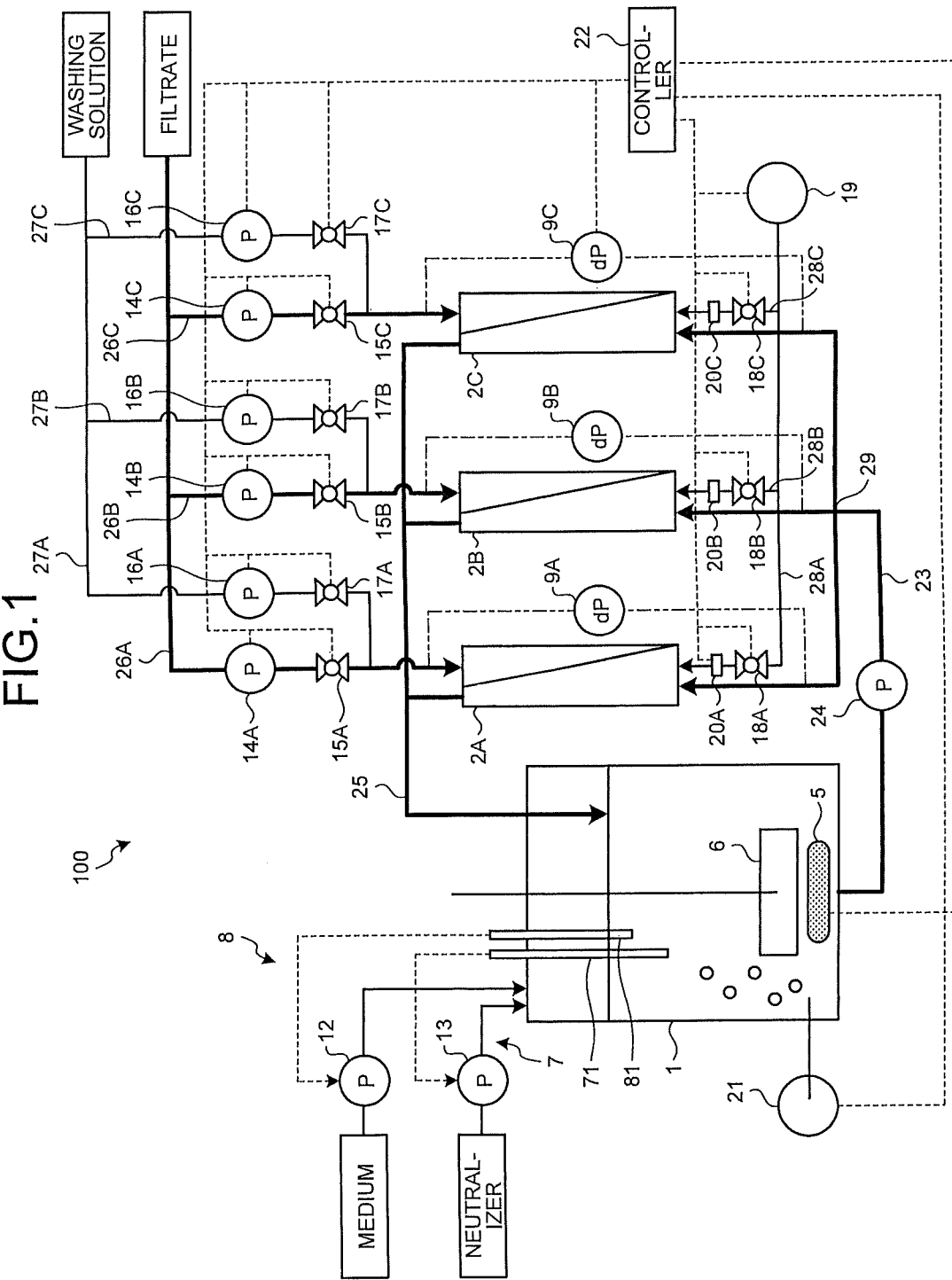
FIG. 1 is a schematic diagram illustrating one example of a continuous fermentation apparatus.

REFERENCE SIGNS LIST 1 fermentor
2A, 2B, 2C separation membrane unit
5 temperature control unit
6 stirrer
7 pH control unit
8 level control unit
9 differential pressure control unit
12 culture medium supply pump
13 neutralizer supply pump
14A, 14B, 14C filtration pump
15A, 15B, 15C filtration valve
16A, 16B, 16C washing pump
17A, 17B, 17C washing valve
18A, 18B, 18C gas supply control valve
19 scrubbing gas supply device
20A, 20B, 20C flow meter
21 fermentor gas supply device
22 controller
23, 23A, 23B, 23C pipe
24 circulation pump
25 pipe
26A, 26B, 26C pipe
27A, 27B, 27C pipe
28A, 28B, 28C pipe
29 junction for each separation membrane unit
71 pH sensor
81 level sensor
100, 100A continuous fermentation apparatus

DETAILED DESCRIPTION

Hereinafter, a method of producing a chemical and a continuous fermentation apparatus will be described in detail on the basis of the drawings. Note that this disclosure is not limited to the examples herein.

1. Continuous Fermentation Apparatus

One example of a continuous fermentation apparatus will be described with reference to FIG. 1. FIG. 1 is a schematic view of a continuous fermentation apparatus. In this example, three separation membrane units are connected in parallel. The number of the separation membrane units connected in parallel is not restricted, and is not limited as long as two or more separation membrane units are used.

As shown in FIG. 1, a continuous fermentation apparatus 100 includes a fermentor 1, separation membrane units 2A, 2B, and 2C, and pipes 23 and 25 that connect the fermentor 1 to the separation membrane units 2A, 2B, and 2C. The fermentor 1 and the separation membrane units 2A, 2B, and 2C are connected to one another through the pipes 23 and 25 to construct a circulation system.

The fermentor 1 is configured to contain a culture solution thereinside. Specifically, the fermentor 1 is made of a material having excellent pressure resistance, heat resistance, and fouling resistance. For the fermentor 1, various shapes such as a cylindrical shape and a polygonal cylindrical shape can be used. The fermentor 1 needs to have such a shape capable of being charged with a fermentation raw material, cells, and a solid, a liquid, or a gas necessary for fermentation, and stirring them, being sterilized if necessary, and being sealed. From the viewpoint of stirring efficiency of the culture solution, it is preferable that the fermentor 1 be cylindrical. To prevent germs from entering the fermentor 1 from the outside of the fermentor 1 and proliferating, it is preferable that the inside of the fermentor 1 be maintained in a pressurization state. To control air pressure in the fermentor 1, a mechanism such as a fermentor pressure gauge is provided.

The separation membrane units 2A, 2B, and 2C include a large number of separation membranes such as hollow fiber membranes and flat membranes. The separation membrane units 2A, 2B, and 2C will be described below in detail. Each of the separation membrane units 2A, 2B, and 2C may include a plurality of separation membrane modules connected in series.

The continuous fermentation apparatus 100 includes a controller 22. The controller 22 can conduct various types of calculations. The controller 22 controls operations of each unit in the continuous fermentation apparatus 100 on the basis of detection results of various sensors, inputs by a user, and various settings.

Further, the continuous fermentation apparatus 100 includes a fermentor gas supply device 21, a temperature control unit 5, a stirrer 6, a pH control unit 7, and a level control unit 8 as mechanisms mainly involved in a fermentation process.

The fermentor gas supply device 21 supplies a gas into the fermentor 1. The supplied gas may be collected and supplied into the fermentor 1 again by the fermentor gas supply device 21.

It is preferable that the pressure in the fermentor 1 be kept higher than the outside air pressure to suppress contamination of germs.

The temperature control unit 5 includes a temperature sensor and a temperature adjustment unit. The temperature sensor detects the temperature of the culture solution in the fermentor 1. The temperature adjustment unit is operated under control by the controller 22 so that a result detected by the temperature sensor falls within a certain range. Thus, a temperature environment suited for fermentation or cell proliferation is maintained by keeping the temperature in the fermentor 1 constant. The temperature adjustment unit can have one or both of heating and cooling functions.

The stirrer 6 stirs the culture solution in the fermentor 1 to maintain a suitable fermentation environment.

The pH control unit 7 includes a pH sensor 71 and a neutralizer supply pump 13. The pH sensor 71 detects the pH of the culture solution in the fermentor 1. The neutralizer supply pump 13 is disposed on a pipe that connects a neutralizer tank to the fermentor 1, and adds a neutralizer to the fermentor 1. The neutralizer supply pump 13 is operated under control by the controller 22 so that a result detected by the pH sensor 71 falls within a certain range. As the neutralizer, an acid and/or an alkali are used.

The level control unit 8 includes a level sensor 81 and a culture medium supply pump 12. The culture medium supply pump 12 is disposed on a pipe that connects a culture medium tank to the fermentor 1. When a result detected by the level sensor 81 shows that the amount of the culture solution in the fermentor 1 is lower than a predetermined lower limit, the culture medium supply pump 12 is operated under control by the controller 22 to supply the culture medium to the fermentor 1. Operation of the culture medium supply pump 12 is stopped when the result shows that the amount of the culture solution reaches an upper limit. Thus, the amount of the culture solution in the fermentor 1 is appropriately maintained.

The continuous fermentation apparatus 100 has a circulation system to circulate the culture solution between the fermentor 1 and the separation membrane modules 2A, 2B, and 2C. Specifically, the continuous fermentation apparatus 100 includes the pipe 23 that connects the fermentor 1 to the primary sides of the separation membrane units 2A, 2B, and 2C, and the pipe 25 of returning to the fermentor 1 a retentate that has not permeated separation membranes of the separation membrane units 2A, 2B, and 2C. Since the pipe 23 connects to the lower portions of the separation membrane units 2A, 2B, and 2C, the culture solution is supplied from the lower portions of the separation membrane units 2A, 2B, and 2C. A circulation pump 24 is disposed on the pipe 23 to supply the culture solution to the separation membrane units 2A, 2B, and 2C from the fermentor 1. The circulation pump 24 is operated to deliver the culture solution from the fermentor 1 toward the separation membrane units 2A, 2B, and 2C.

The continuous fermentation apparatus 100 includes a pipe 26A connected to the separation membrane unit 2A and configured to discharge a filtrate (i.e., permeate) out of the apparatus. On the pipe 26A, a filtration pump 14A is provided, and a filtration valve 15A is further provided. Similarly, pipes 26B and 26C, filtration valves 15B and 15C, and filtration pumps 14B and 14C are provided for the separation membrane units 2B and 2C, respectively. The filtration valve 15A is disposed between the filtration pump 14A and the separation membrane unit 2A. However, our methods and apparatus are not limited to this arrangement.

The continuous fermentation apparatus 100 has a configuration for back pressure washing the separation membrane unit 2A. Back pressure washing means that a separation membrane is washed by passing a liquid for washing (hereinafter sometimes referred to as "washing solution") from the secondary side of the separation membrane to the primary side thereof. The continuous fermentation apparatus 100 includes a washing solution tank configured to contain a washing solution, a pipe 27A to connect the washing solution tank to the secondary side of the separation membrane unit 2A, a washing pump 16A disposed on the pipe 27A, and a washing valve 17A. A washing solution is delivered toward the separation membrane unit 2A by the washing pump 16A. On the pipe 27A, a pressure gauge, a flow meter, a device for sterilization, a filter for sterilization, and the like may be provided. Similarly, pipes 27B and 27C each connecting the washing solution tank to the secondary side of the separation membrane unit, washing pumps 16B and 16C, and washing valves 17B and 17C are provided for the separation membrane units 2B and 2C, respectively. The washing valve 17A is disposed between the washing pump 16A and the separation membrane unit 2A. However, our methods and apparatus are not limited to this arrangement.

A differential pressure control unit 9A can detect a transmembrane pressure difference (TPD) of the separation membrane unit 2A. Specifically, a pressure difference between the primary side (side in which a culture solution is supplied) and the secondary side (side in which a permeate, that is, a filtrate is discharged) of the separation membrane unit 2A is detected. Similarly, differential pressure control units 9B and 9C are provided for the separation membrane units 2B and 2C, respectively.

Further, the continuous fermentation apparatus 100 has a configuration involved in scrubbing. Scrubbing is a washing method in which a gas is supplied to the primary sides of the separation membrane units 2A, 2B, and 2C and substances attached to a surface of the separation membranes are removed from the surface of the separation membranes by shaking of a liquid and a gas generated during passing of the gas through the separation membrane units. Hereinafter, in the separation membrane modules 2A, 2B, and 2C, a side to come in contact with a stock solution to be treated is referred to as the primary side, and a side to come in contact with a treated filtrate is referred to as the secondary side.

Figure 2:
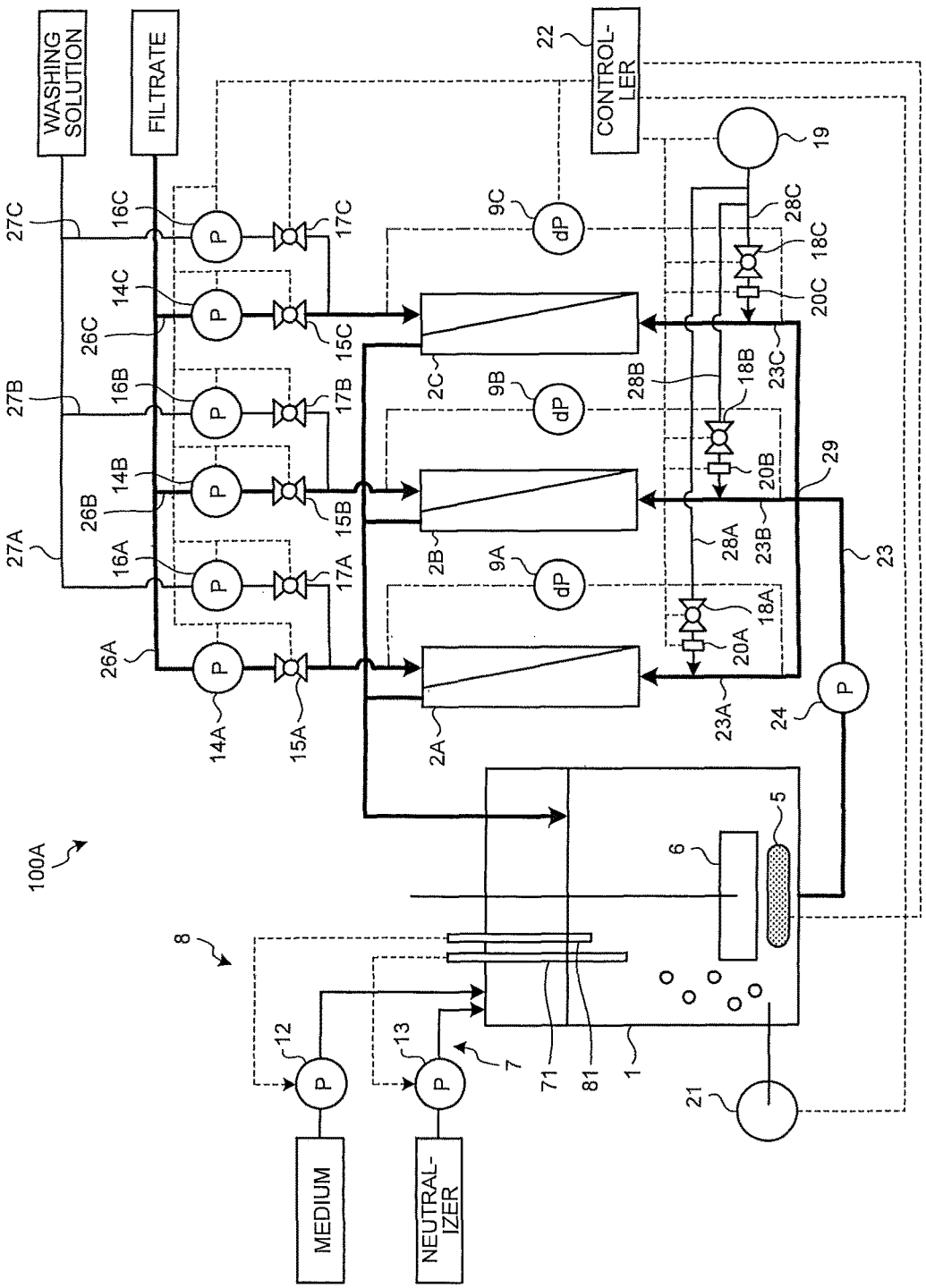
FIG. 2 is a schematic diagram illustrating one example of a continuous fermentation apparatus according to a modification.

In the continuous fermentation apparatus 100, a gas is supplied, especially to the separation membrane unit 2A through any of the lower portion of modules in the membrane unit and, as shown in FIG. 2, the middle of a pipe that connects a junction 29 for each membrane unit to the membrane unit. As the configuration involved in scrubbing, a gas supply source, a gas supply port, and a mechanism capable of adjusting the supply rate of a gas from the gas supply source are especially provided.

Specifically, the separation membrane unit 2A is provided with a gas supply control valve 18A and a flow meter 20A. Similarly, the separation membrane units 2B and 2C are each provided with a gas supply control valve 18B or 18C and a flow meter 20B or 20C. A gas is supplied from a scrubbing gas supply device 19 to the separation membrane units 2A, 2B, and 2C through pipes 28A, 28B, and 28C. The scrubbing gas supply device 19 may be provided to each of the separation membrane units 2A, 2B, and 2C. When a plurality of separation membrane modules are arranged in series in each of the separation membrane units 2A, 2B, and 2C, the scrubbing gas supply device 19 may be provided to each of the separation membrane modules, or the scrubbing gas supply device 19 may be commonly used for a plurality of units and modules.

The scrubbing gas supply device 19 connects to the separation membrane units 2A, 2B, and 2C on the primary side of the separation membranes, that is, on the side in which a culture solution is supplied, through the pipes 28A, 28B, and 28C. The pipes 28A, 28B, and 28C are different from the pipe 23 that supplies a culture solution to the separation membrane unit 2. The pipes 28A, 28B, and 28C directly connect to the lower portions of the separation membrane modules in the separation membrane units 2A, 2B, and 2C. As shown in the modification of FIG. 2, the pipes 28A, 28B, and 28C may connect to the middle of pipes 23A, 23B, and 23C that each connect the junction 29 for each of the separation membrane units 2A, 2B, and 2C to each of the separation membrane units 2A, 2B, and 2C. The "lower portion" herein may mean a bottom portion of a separation membrane module or a portion within one third of the height from the bottom surface of the separation membrane module. The scrubbing gas supply device 19 can send a gas to the separation membrane units 2A, 2B, and 2C through the pipes 28A, 28B, and 28C. The gas supply control valves 18A, 18B, and 18C are disposed on the pipes 28A, 28B, and 28C, respectively, and can adjust the amount of a gas to be supplied to the separation membrane units 2A, 2B, and 2C, respectively, by opening and closing. A device for sterilization, a filter for sterilization, and the like may be provided in the pipes 28A, 28B, and 28C to prevent germs from entering the fermentor 1.

The gas supply port is a portion from which a gas is released into the culture solution or a liquid. It is preferable that the gas supply port be configured to generate bubbles capable of washing a membrane surface. The generated bubbles may be fine bubbles or coarse bubbles. The size of the bubbles is changed by changing the shape of the gas supply port depending on conditions such as the kinds of separation membranes and the amount of diffused gas. The gas supply port may be configured to provide an air discharge hole on a pipe made of vinyl chloride or stainless steel. Alternatively, an air diffusion pipe made of a porous rubber, ceramic, or membrane may be used. The size of the gas supply port is not limited as long as it can supply a specific amount of a gas and be enough not to cause clogging by a fermentation liquid. The gas supply port may be equipped with a filter for sterilization to prevent germs from entering a fermentation system.

The gas supply port is provided at an end part of both end parts of each of the pipes 28A, 28B, and 28C, on a side near the separation membrane units 2A, 2B, and 2C, that is, in the lower portion of the separation membrane modules. In other words, the pipes 28A, 28B, and 28C are pipes connecting from the gas supply source to the gas supply port.

The gas supply port may be provided in the lower portion of the separation membrane modules. When the pipes 28A, 28B, and 28C are connected to the middle of the pipes 23A, 23B, and 23C that each connect the junction 29 to each of the separation membrane units 2A, 2B, and 2C, as shown in the modification of FIG. 2, the gas supply port may be provided in connection portions between the pipes 28A, 28B, and 28C and the pipes 23A, 23B, and 23C.

As an example of a mechanism that measures a linear velocity of a gas supplied by the scrubbing gas supply device 19, flow meters 20A, 20B, and 20C are shown. The flow meters 20A, 20B, and 20C are provided on the pipes 28A, 28B, and 28C, respectively, and can measure the flow rate of a gas passing through the pipes 28A, 28B, and 28C. The flow meters 20A, 20B, and 20C are utilized to measure the linear velocity of a gas supplied to the separation membrane units 2A, 2B, and 2C by the pipe scrubbing gas supply device 19.

2. Separation Membrane Unit and Module

The separation membrane units 2A, 2B, and 2C each represent a unit of separation membrane to which a gas is simultaneously supplied through the same valve, and include one separation membrane module or two or more separation membrane modules connected in series.

The separation membrane module in the separation membrane units 2A, 2B, and 2C has a separation membrane and a case housing the separation membrane.

The separation membrane used for the separation membrane module may be an organic membrane or an inorganic membrane. The separation membrane is not limited as long as it is a membrane usable for filtration of a culture solution and having durability against washing with a gas. Examples of the separation membrane may include membranes made of polyvinylidene fluoride, of polysulfone, of polyethersulfone, of polytetrafluoroethylene, of polyethylene, of polypropylene, and of ceramics. A separation membrane made of polyvinylidene fluoride is particularly preferable since fouling due to a fermentation liquid is unlikely to be generated, washing is easy, and durability against washing with a gas is excellent.

It is preferable that the separation membrane be a porous film having micropores with an average pore diameter of 0.001 μm or more and less than 10 μm to effectively separate cells in a fermentation liquid. As the shape of the separation membrane, any shape such as a flat membrane and a hollow fiber membrane can be used. A hollow fiber membrane having a larger membrane area relative to the volume of the module is preferable. The average pore diameter of a membrane is determined according to a method described in ASTM: F316-86 (another name: half dry method). An average pore diameter determined by this half dry method is the average pore diameter of a layer of a membrane with a minimum pore diameter.

Standard measurement conditions in measurement of average pore diameter by the half dry method are as follows:
Liquid used: ethanol
Measurement temperature: 25° C.
Pressure rising rate: 1 kPa/second.

An average pore diameter [μm] is determined from the following equation:

Average pore diameter [μm]=(2860×surface tension [mN/m])/half dry air pressure [Pa].

The surface tension of ethanol at 25° C. is 21.97 mN/m (The Chemical Society of Japan Ed, Kagaku Binran Kisohen Kaitei sanpan, p. II-82, Maruzen, 1984) so that under the standard measurement conditions, the average pore diameter can be determined from the equation: average pore diameter [μm]=62834.2/(half dry air pressure [Pa]).

The outer diameter of an external pressure type hollow fiber membrane is desirably 0.5 mm or more and 3 mm or less. When the outer diameter is 0.5 mm or more, resistance of a filtrate flowing in the hollow fiber membrane can be decreased to a relatively low level. Further, when the outer diameter is 3 mm or less, the hollow fiber membrane can be prevented from being collapsed by the external pressure due to a fermentation liquid or gas.

The inner diameter of an inner pressure type hollow fiber membrane is desirably 0.5 mm or more and 3 mm or less. When the inner diameter is 0.5 mm or more, resistance of a fermentation liquid flowing in the hollow fiber membrane can be decreased to a relatively low level. Further, when the inner diameter is 3 mm or less, a membrane surface area can be ensured and, therefore, an increase in the number of modules used can be suppressed.

The case of the separation membrane module is made of a material having excellent pressure resistance. The shape thereof is not limited as long as it enables supply of a fermentation liquid to the primary side of the module, and includes a cylindrical shape and a polygonal columnar shape. In consideration of the flow and handling property of a fermentation liquid, the case is preferably cylindrical.

3. Method of Producing Chemical

The production method may be a method of producing a chemical by continuous fermentation including the following steps (a) to (e):
(a) a chemical production step of culturing cells in a culture solution in a fermentor to ferment a feedstock to produce a chemical;
(b) a culture solution supply step of supplying the culture solution containing the chemical produced in the chemical production step to a plurality of separation membrane units arranged in parallel;
(c) a filtration step of filtering the culture solution supplied in the culture solution supply step to isolate a permeate containing the chemical;
(d) a reflux step of refluxing a retentate that is not filtered in the filtration step to the fermentor; and
(e) a washing step of supplying a gas containing oxygen to the plurality of separation membrane units while a supply amount is changed to at least two different values to perform scrubbing.

The production method may be characterized in that the supply amount and time of the gas containing oxygen to be supplied in the chemical production step and the washing step are set so that a kLa is within a predetermined range from an optimal kLa value for the cells cultured in the chemical production step. Each step will be described below. The steps (a) to (d) may also be called a continuous culture process or a continuous fermentation process.

3-1. Chemical Production Step

Cell

The "cells" used herein means a concept including microorganisms and cultured cells, and eukaryotic cells and prokaryotic cells. As the microorganisms, yeast often used in fermentation industry such as baker's yeast; bacteria such as *Escherichia coli*, lactic acid bacteria, and coryneform bacteria; filamentous fungi; actinomycetes; or the like are used. The cultured cells are cells derived from a multicellular organism and examples thereof may include animal cells and insect cells. Cells to be used for the production of a chemical may be those isolated from a natural environment or those having properties partly modified by mutation or gene recombination. Cells are selected depending on a target chemical, a raw material, a culture condition, and the like.

Eukaryotic cells have a structure called cell nucleus (nucleus) therein and clearly discriminated from a prokaryotic organism having no cell nucleus (hereinafter simply referred to as "nucleus"). For the production of a chemical, among eukaryotic cells, yeast can be preferably used. Examples of yeast suitable for the production of a chemical may include yeast belonging to the genus *Saccharomyces*. Among them, *Saccharomyces cerevisiae* is a particularly preferable species.

Prokaryotic cells do not have a structure called cell nucleus (nucleus) therein and are clearly discriminated from a eukaryotic organism having a cell nucleus (nucleus). For example, among prokaryotic cells, lactic acid bacteria can be preferably used for the production of a chemical.

Examples of L-amino acid-producing cells may include bacteria often used in the fermentation industry such as *Escherichia coli* and coryneform bacteria. Specific examples of L-threonine-producing bacteria may include bacteria belonging to the genus *Escherichia*, the genus *Providencia*, the genus *Corynebacterium*, the genus *Brevibacterium*, and the genus *Serratia*. Among them, *Escherichia coli*, *Providencia rettgeri*, *Corynebacterium glutamicum*, *Brevibacterium flavum*, *Brevibacterium lactofermentum*, and *Serratia marcescens* are particularly preferable species.

Examples of L-lysine-producing bacteria may include bacteria belonging to the genus *Escherichia*, the genus *Corynebacterium*, and the genus *Brevibacterium*. Among them, *Escherichia coli*, *Corynebacterium glutamicum*, *Brevibacterium flavum*, and *Brevibacterium lactofermentum* are particularly preferable bacteria.

It is preferable that L-glutamic acid-producing bacteria be *Corynebacterium glutamicum*, *Brevibacterium flavum*, or *Brevibacterium lactofermentum*.

Examples of L-tryptophan-producing bacteria may include *Corynebacterium glutamicum*, *Brevibacterium flavum*, *Brevibacterium lactofermentum*, *Bacillus subtilis*, *Bacillus amyloliquefaciens*, and *Escherichia coli*.

Examples of L-isoleucine-producing bacteria may include *Corynebacterium glutamicum*, *Brevibacterium flavum*, *Brevibacterium lactofermentum*, and *Serratia marcescens*.

Examples of L-glutamine-producing bacteria may include *Corynebacterium glutamicum*, *Brevibacterium flavum*, *Brevibacterium lactofermentum*, and *Flavobacterium rigense*.

Examples of L-arginine-producing bacteria may include *Corynebacterium glutamicum*, *Brevibacterium flavum*, *Serratia marcescens*, *Escherichia coli*, and *Bacillus subtilis*.

Examples of L-alanine-producing bacteria may include *Brevibacterium flavum* and *Arthrobacter oxydans*.

Examples of L-histidine-producing bacteria may include *Corynebacterium glutamicum*, *Brevibacterium flavum*, *Brevibacterium ammoniagenes*, *Serratia marcescens*, *Escherichia coli*, *Bacillus subtilis*, and *Streptomyces coelicolor*.

Examples of L-proline-producing bacteria may include *Corynebacterium glutamicum*, *Kurthia catenaforma*, *Serratia marcescens*, and *Escherichia coli*.

Examples of L-phenylalanine-producing bacteria may include *Corynebacterium glutamicum*, *Brevibacterium flavum*, *Brevibacterium lactofermentum*, and *Escherichia coli*.

Examples of L-aspartic acid-producing bacteria may include *Brevibacterium flavum*, *Bacillus megatherium*, *Escherichia coli*, and *Pseudomonas fluorescens*.

Examples of L-tyrosine-producing bacteria may include *Corynebacterium glutamicum*, *Brevibacterium flavum*, *Brevibacterium lactofermentum*, and *Escherichia coli*.

Examples of L-methionine-producing bacteria may include *Escherichia coli* and *Corynebacterium glutamicum*.

Examples of L-serine-producing bacteria may include *Escherichia coli*, *Corynebacterium glutamicum*, *Brevibacterium flavum*, *Arthrobacter oxydans*, *Corynebacterium acetoacidophilum*, and *Brevibacterium lactofermentum*.

Examples of L-valine-producing bacteria may include *Brevibacterium lactofermentum*, *Serratia marcescens*, and *Klebsiella pneumoniae*.

Examples of L-leucine-producing bacteria may include *Corynebacterium glutamicum*, *Brevibacterium lactofermentum*, and *Serratia marcescens*.

A microorganism having L-amino acid production ability may be one isolated from the natural environment or one having properties partly modified by mutation or gene recombination. Examples thereof may include *Providencia rettgeri* having improved L-threonine productivity, described in Japanese Laid-open Patent Publication No. 2-219582 and *Corynebacterium glutamicum* having improved L-alanine productivity, described in Japanese Laid-open Patent Publication No. 3-500486.

Separation and purification of L-amino acid contained in a culture solution can be performed using conventionally known methods such as filtration, concentration, distillation, and crystallization in combination.

When D-lactic acid is produced, cells of wild-type strain having enhanced enzyme activity of D-lactate dehydrogenase are preferably used. As a method of enhancing enzyme activity, a conventionally known method by chemical mutagenesis can also be employed. When a gene encoding D-lactate dehydrogenase (hereinafter sometimes referred to as D-LDH) is incorporated in cells, the enzyme activity of D-lactate dehydrogenase can be imparted or enhanced. Therefore, recombinant cells are also suitably used for the production of a chemical.

When D-lactic acid is produced using recombinant cells, it is preferable that host cells be *Escherichia coli* as prokaryotic cells or yeast as eukaryotic cells, and particularly preferably yeast. Of the yeast, yeast belonging to the genus *Saccharomyces* is preferable, and *Saccharomyces cerevisiae* is more preferable. In particular, yeast showing a yield per sugar of 50% or more is preferable. The yield per sugar means a ratio of the production amount of lactic acid to the total amount of sugar consumed.

The sequence of D-LDH is not limited to a specific sequence as long as it encodes a protein having activity of converting reduced nicotinamide adenine dinucleotide (NADH) and pyruvic acid into oxidized nicotinamide adenine dinucleotide (NAD+) and D-lactic acid. For example, it is preferable that D-LDH be a gene derived from

*Lactobacillus plantarum, Pediococcus acidilactici, Bacillus laevolacticus, Limulus polyphemus, Tachypleus tridentatus, Tachypleus gigas*, or *Tachypleus rotundicauda*, and more preferably a gene derived from *Bacillus laevolacticus* or *Limulus polyphemus*.

When L-lactic acid is produced, cells of wild-type strain having enhanced enzyme activity of L-lactate dehydrogenase are preferably used. As the method of enhancing enzyme activity, the conventionally known method by chemical mutagenesis can also be employed. Cells to which lactic acid production ability is artificially imparted or artificially enforced can be used. For example, L-lactic acid production ability can be imparted or enforced by introducing an L-lactate dehydrogenase gene (hereinafter sometimes referred to as "L-LDH") into cells. Therefore, recombinant cells are also suitably used.

When L-lactic acid is produced using recombinant cells, it is preferable that the host cells be *Escherichia coli* as prokaryotic cells or yeast as eukaryotic cells. In particular, yeast is preferably used. Of the yeast, yeast belonging to the genus *Saccharomyces* is preferable, and *Saccharomyces cerevisiae* is more preferable.

The sequence of L-LDH is not limited to a specific sequence as long as it encodes a protein having activity of converting reduced nicotinamide adenine dinucleotide (NADH) and pyruvic acid into oxidized nicotinamide adenine dinucleotide (NAD+) and L-lactic acid. For example, as L-LDH, a gene derived from lactic acid bacteria having a high yield per sugar, derived from a mammal, or derived from a frog can be used. As the gene derived from a mammal, L-LDH derived from *Homo sapiens* can be suitably used. As the gene derived from a frog, L-LDH derived from a frog belonging to the family Pipidae can be particularly preferably used, and in particular, L-LDH derived from *Xenopus laevis*, among frogs belonging to the family Pipidae, can be preferably used.

D-LDH and L-LDH include a genetically polymorphic gene and a mutated gene obtained by mutagenesis or the like. The genetically polymorphic gene means a gene having a base sequence partially changed by spontaneous mutation on the gene. The mutagenesis means artificial introduction of mutation into a gene. The mutagenesis is achieved, for example, by a method using a kit for introducing site-specific mutagenesis (Mutan-K (manufactured by Takara Bio)), a method using a kit for introducing random mutagenesis (BD Diversify PCR Random Mutagenesis (manufactured by CLONTECH)), or the like. D-LDH and L-LDH may have a base sequence partially defected or inserted as long as they encode a protein having activity of converting NADH and pyruvic acid into NAD+ and lactic acid.

The production of pyruvic acid will be described. Examples of pyruvic acid producing cells may include bacteria belonging to the genus *Pseudomonas*, the genus *Corynebacterium*, the genus *Escherichia*, and the genus *Acinetobacter*. Bacteria such as *Pseudomonas fluuorescens, Pseudomonas aeruginosa*, and *Escherichia coli* are more preferable. Further, bacteria having properties partially modified by mutation or genetic recombination may be used. For example, bacteria obtained by mutating or deleting an ATPase gene directly involved in ATP production by oxidative phosphorylation are also preferably used.

Fungi and yeast are also preferably used. For example, fungi and yeast that belong to the genus *Saccharomyces*, the genus *Toluropusis*, the genus *Candida*, or the genus *Schizophyllum* can be used. Fungi and yeast including *Saccharomyces cerevisiae, Saccharomyces copsis, Candida glabrata,* *Candida lipolytica, Toluropusis glabrata*, and *Schizophyllum commune* can be more preferably used to produce pyruvic acid.

Separation and purification of pyruvic acid contained in a culture solution can be performed by a method using filtration and an anion exchange column. For example, a purification method using a weakly basic ion exchanger described in Japanese Laid-open Patent Publication No. 6-345683 can be suitably used.

Production of itaconic acid will be described. As itaconic acid producing cells, for example, fungi or yeast can be preferably used. Preferable examples thereof may include fungi belonging to the genus *Aspergillus* and the genus *Ustilago* and yeast belonging to the genus *Candida* and the genus *Rhodotorula*. In particular, fungi such as *Aspergillus terreus, Aspergillus itaconicus, Ustilago maydis, Ustilago cynodontis*, and *Ustilago rabenhorstina*, or *Candia antarctica* can be preferably used for the production of itaconic acid.

Production of cadaverine will be described. As cells capable of producing cadaverine, a microorganism having enhanced enzyme activity of a lysine decarboxylase and/or a lysine-cadaverine antiporter is preferable. More preferable examples thereof may include a recombinant microorganism in which a gene encoding a lysine decarboxylase and/or a lysine-cadaverine antiporter is incorporated. Further preferable examples thereof may include a recombinant microorganism in which one or two or more kinds of genes encoding a lysine decarboxylase are incorporated.

When cadaverine is produced, it is preferable that the recombinant microorganism be *Escherichia coli* or coryneform bacteria, and more preferably coryneform bacteria having lysine decarboxylase activity and at least one property of homoserine auxotrophy and resistance to S-(2-aminoethyl)-L-cysteine. It is more preferable that the microorganism be deficient in homoserine dehydrogenase activity, and more preferably deficient in homoserine dehydrogenase activity by formation of gene insertion mutation. It is preferable that the genus of coryneform bacteria be at least one genus selected from the group consisting of the genus *Corynebacuterium* and the genus *Brevibacterium*. *Corynebacuterium gulutamicum* is more preferable.

Culture Medium

A fermentation raw material (hereinafter simply referred to as "feedstock") is a substance from which a target chemical is obtained by fermentation. The feedstock may be changed depending on cells, culture conditions, the target chemical, and the like.

A culture medium to be used for culture contains a component capable of accelerating growth of cells to well produce a chemical as a target fermentation product, in addition to the feedstock. The "culture medium" used herein represents a liquid culture medium unless otherwise specifically indicated. For example, the culture medium contains a carbon source, a nitrogen source, an inorganic salt and, if necessary, organic micronutrients such as amino acid and vitamin.

Examples of the carbon source used may include saccharides such as glucose, sucrose, fructose, galactose, and lactose; starches containing the saccharides, a starch hydrolysate, sweet potato molasses, beet molasses, and cane juice; extracts and concentrated liquid obtained from beet molasses or cane juice; filtrates of beet molasses or cane juice; syrup (high-test molasses); raw material saccharides obtained by purification or crystallization of beet molasses or cane juice; purified saccharides obtained by purification or crystallization of beet molasses or cane juice; organic acids such as acetic acid and fumaric acid; alcohols such as ethanol; and glycerol. The saccharides used herein mean a carbohydrate that is a first oxidation product of polyhydric alcohol, has an aldehyde group or a ketone group, and is classified into aldose that is a saccharide having an aldehyde group and ketose that is a saccharide having a ketone group.

As the nitrogen source, for example, ammonia gas, aqueous ammonia, ammonium salts, urea, nitrate salts, and other organic nitrogen sources secondarily used are used. For example, oil cake, a hydrolyzed soy liquid, a casein decomposition product, another amino acid, vitamin, corn steep liquor, yeast or a yeast extract, a meat extract, peptides such as peptone, various types of fermentation cells, or hydrolysates thereof are used.

As the inorganic salts, for example, a phosphate, a magnesium salt, a calcium salt, an iron salt, a manganese salt, or the like can be appropriately used.

Culture Solution

A culture solution contains a culture medium and cells to be cultured therein, and may also contain a chemical produced as a result of the culture.

A filtrate obtained using a separation membrane module does not substantially contain cells, but for the sake of convenience of description, the filtrate may also be called a culture solution.

Culture

In the continuous fermentation apparatus 100, continuous culture is performed by extracting a culture solution from the fermentor 1 while the feedstock is supplied to the fermentor 1.

Batch culture or fed-batch culture is performed at an early stage of culture to increase the cell concentration, and continuous culture may be then initiated. At this time, the cells may be extracted if necessary. Highly concentrated cells are inoculated and continuous culture may be performed along with initiation of culture.

Introduction of the feedstock will be described. In FIG. 1, when the culture medium supply pump 12 is operated during culture, a culture medium is introduced into the fermentor 1 and as a result, the feedstock is introduced.

While culturing is performed, introduction of the feedstock may be always performed without stopping, or the introduction of the feedstock and stopping of the introduction may be switched according to the situation. For example, as described above, the initiation and stop of introduction of a culture medium may be performed on the basis of detection results of the level sensor 81, or may be performed at certain time intervals on the basis of measurement results using a timer, which is not shown. Both automatic and manual introductions of the feedstock are possible.

Next, extraction of a culture solution will be described. To achieve efficient productivity, it is preferable that the concentration of cells in a culture solution be maintained high so that the ratio leading to death is not increased by an environment of the culture solution that is inappropriate for proliferation of a microorganism or cultured cells.

In the continuous fermentation apparatus 100, continuous culture can be performed while a culture solution is extracted by a circulation system to collect a chemical and the cell concentration is maintained high. Extraction of a culture solution by the circulation system will be described below in detail.

In addition to the pipe 23 connected to the separation membrane units 2A, 2B, and 2C, a flow channel for extraction may connect to the fermentor 1, and a culture solution may be extracted through this flow channel for extraction. At this time, not only a liquid portion of the culture solution but also cells may be extracted.

During culture, fresh cells may be introduced into the fermentor 1. The cells may be introduced either manually or automatically.

In the fermentor 1, initiation times of supply of the feedstock and extraction of a culture solution may not be necessarily the same. The supply of the feedstock and the extraction of a culture solution may be performed successively or intermittently.

It is preferable that continuous culture operation be usually performed in a single fermentor 1 for the purpose of control. However, the number of fermentor 1 is not limited as long as a continuous fermentation culture method in which a product is produced under proliferation of cells is used. A plurality of fermentors 1 may be used because of the small capacity of the fermentor 1 or other reasons. In this case, high productivity can be achieved even by continuous culture in a plurality of fermentors 1 connected in parallel or in series through pipes.

In the continuous fermentation apparatus 100 of FIG. 1, a culture solution in the fermentor 1 is stirred by the stirrer 6 and a condition suitable for fermentation is maintained by the temperature control unit 5, the pH control unit 7, and the level control unit 8.

Culture of cells can be usually performed at pH of 3 or more and 10 or less and a temperature of 15° C. or higher and 65° C. or lower. The pH of the culture solution is adjusted within a predetermined range in the above-mentioned range by an inorganic or organic acid, an alkaline substance, urea, calcium hydroxide, calcium carbonate, ammonia gas, or the like. In the continuous fermentation apparatus 100, under control of the controller 22, the pH is automatically controlled by the pH control unit 7, and the temperature is automatically controlled by the temperature control unit 5.

3-2. Culture Solution Filtration Step

Through a filtration step, a chemical can be continuously collected from the culture solution and culture can be continued. Specifically, in FIG. 1, the culture solution is extracted from the fermentor 1 by the circulation pump 24, and then supplied through the pipe 23 to the separation membrane units 2A, 2B, and 2C. The culture solution is separated into a retentate and a permeate by the separation membrane units 2A, 2B, and 2C.

The circulation pump 24 in FIG. 1 corresponds to a crossflow circulation pump and crossflow filtration is performed in the separation membrane units 2A, 2B, and 2C. Dead end filtration may be employed as a membrane filtration method. However, in the continuous fermentation operation, a large amount of fouling such as microorganisms is attached to a membrane. Therefore, it is preferable that crossflow filtration be performed to effectively remove the fouling. This is because in the crossflow filtration, the fouling can be removed by a shearing force of the culture solution. By combining the crossflow filtration with scrubbing, higher washing efficiency can be accomplished.

A driving force of filtration may be obtained using a siphon that utilizes a level difference (water head difference) between the fermentor 1 and the separation membrane units 2A, 2B, and 2C, or obtained using a transmembrane pressure difference caused by the crossflow circulation pump. For the driving force of filtration, a suction pump may be provided on a filtrate side of the separation membrane units 2A, 2B, and 2C. In the example of FIG. 1, the filtration pumps 14A, 14B, and 14C correspond to a suction pump.

When the crossflow circulation pump is used, a transmembrane pressure difference can be controlled by the pressure of the suction pump. Further, the transmembrane pressure difference can be controlled by the pressure of a gas or a liquid to be introduced into the primary sides of the separation membrane units 2A, 2B, and 2C. A difference between the pressure on the primary sides of the separation membrane units 2A, 2B, and 2C and the pressure on the filtrate side is detected as the transmembrane pressure difference. Control of the pump, and the like can be performed in accordance with this transmembrane pressure difference.

In the configuration of FIG. 1, the culture solution is supplied from the fermentor 1 to the separation membrane units 2A, 2B, and 2C by the circulation pump 24. The operations of the circulation pump 24 and the filtration pumps 14A, 14B, and 14C are controlled in accordance with the transmembrane pressure difference detected by the differential pressure control unit 9A, 9B, and 9C, to appropriately adjust the amount of culture solution to be supplied to the separation membrane units 2A, 2B, and 2C.

Filtration can be performed either continuously or intermittently. When filtration is performed intermittently, filtration can be stopped for a predetermined time (for example, 0.1 to 10 minutes) whenever filtration is performed continuously, for example, for 5 to 120 minutes. It is more preferable that filtration be stopped for 0.25 to 3 minutes whenever filtration is continued for 5 to 10 minutes. As described below, scrubbing may be performed either during stop of filtration or during filtration.

3-3. Separation and Circulation Step

Since cells in the culture solution do not permeate the separation membrane, the concentration of cells in a retentate (liquid that has not permeated) that has passed through the separation membrane units 2A, 2B, and 2C increases. Since the retentate is returned to the fermentor 1 through the pipe 25, the cells are retained in the fermentor 1. The filtrate that has permeated the separation membranes of the separation membrane units 2A, 2B, and 2C is discharged out of the apparatus through the pipes 26A, 26B, and 26C.

Thus, the concentration of cells in the fermentor 1 is maintained at a high level and a chemical is continuously separated from the culture system.

3-4. Gas Supply Step

The whole amount of the gas may be supplied to the fermentor 1 through the separation membrane units 2A, 2B, and 2C, or part of the gas may be directly supplied to the fermentor 1. In consideration of the washing effect of the separation membrane units 2A, 2B, and 2C and an optimal kLa value as described below, it is particularly preferable that an appropriate amount of the gas be supplied to the fermentor 1 through the separation membrane units 2A, 2B, and 2C by the scrubbing gas supply device 19 and the rest of the gas be directly supplied to the fermentor 1.

In the configuration shown in FIG. 1, the step of supplying a gas to the fermentor 1 can be performed using the fermentor gas supply device 21 and the stirrer 6.

On the other hand, a scrubbing gas is supplied to the separation membrane units 2A, 2B, and 2C by the scrubbing gas supply device 19. The gas supplied removes fouling from the separation membranes of the separation membrane units 2A, 2B, and 2C.

The number of scrubbing gas supply devices 19 relative to a plurality of separation membrane units 2A, 2B, and 2C may be one or more. The supply of a gas to each of the separation membrane units 2A, 2B, and 2C by one scrubbing gas supply device 19 is switched by gas supply control valves 18A, 18B, and 18C, and the like.

In the configuration shown in FIG. 1, when scrubbing is initiated, the gas supply control valves 18A, 18B, and 18C are opened by control of the controller 22, a timer, or the like. When scrubbing is stopped, the gas supply control valves 18A, 18B, and 18C are closed similarly by the control of the controller 22, the timer, or the like.

During scrubbing, a liquid such as a culture solution is also supplied to the separation membrane units 2A, 2B, and 2C. A high washing effect can be obtained by combining a washing effect by scrubbing with a washing effect by a liquid flow in the separation membrane units 2A, 2B, and 2C.

In particular, in the configuration of FIG. 1, the culture solution is supplied from the fermentor 1 to the separation membrane units 2A, 2B, and 2C during scrubbing. Specifically, when a scrubbing gas is supplied, the circulation pump 24 is operated. At this time, the filtration pumps 14A, 14B, and 14C may be stopped and at the same time, the filtration valves 15A, 15B, and 15C may be closed, that is, filtration may be stopped. Alternatively, the filtration pumps 14A, 14B, and 14C may be operated, and at the same time, the filtration valves 15A, 15B, and 15C may be opened.

Thus, a high washing effect can be obtained due to the shearing force generated by the flow of the culture solution and the washing effect by scrubbing. A liquid supplied to the separation membrane units 2A, 2B, and 2C during supply of a gas is not limited to the culture solution. Other than the culture solution, for example, a liquid that does not inhibit fermentation such as a culture medium not containing cells, can be used.

As a scrubbing gas, a compressed gas supplied by a gas cylinder, a blower, a compressor, or a pipe can be used. As the scrubbing gas supply device 19, a device capable of compressing a gas and supplying the gas at constant pressure, or a tank capable of containing a compressed gas and supplying the gas at constant pressure can be used.

It is preferable that the gas supplied in accordance with scrubbing be a gas containing oxygen, and it may be pure oxygen. The concentration of oxygen can be adjusted by mixing a gas to not adversely affect fermentation such as air, nitrogen, carbon dioxide, methane, and a mixed gas thereof. To increase a supply rate of oxygen, the supply amount is simply increased. Alternatively, means for keeping the oxygen concentration to 21% or more by adding oxygen to the air, applying a pressure to the culture solution, increasing a stirring rate, or increasing an aeration rate can be used.

An effect of scrubbing washing is to remove fouling such as cells attached to the surface of the separation membranes. By scrubbing washing, a fermentation efficiency can also be improved. The gas supplied in accordance with scrubbing comes into contact with the culture solution, and flows while being in contact with a fermentation liquid in the separation membrane units 2A, 2B, and 2C and the pipe 25. The gas contacts the separation membranes and shakes the membranes in the separation membrane units 2A, 2B, and 2C, flows from the separation membrane units 2A, 2B, and 2C to the fermentor 1 while contacting the fermentation liquid in the pipe 25, and enters the fermentor 1. The gas is stirred in the fermentor 1, and then rises to a space above the surface of the fermentation liquid to complete the contact with the fermentation liquid. On the other hand, when a gas is directly supplied to the fermentor 1, the gas is stirred in the fermentor 1, and immediately rises to a space above the surface of the fermentation liquid to complete the contact with the fermentation liquid. A gas is supplied to the separation membrane units 2A, 2B, and 2C. Therefore, the contact of the gas with the fermentation liquid increases as compared to when a gas containing oxygen is supplied to the fermentor 1. Thus, a larger amount of oxygen can be dissolved in the fermentation liquid to improve the fermentation efficiency.

No specific limitation is imposed on scrubbing conditions, that is, timing of scrubbing, frequency of scrubbing to the separation membrane units 2A, 2B, and 2C, frequency of increasing the flow rate for scrubbing, and time per scrubbing. The scrubbing conditions can be changed depending on various conditions such as a kLa value, a transmembrane pressure difference, change in the transmembrane pressure difference, pressure in the fermentor, the kind of gas to be supplied, the kind of cells to be cultured, the kind of a chemical to be produced, and the kind of the raw materials, as described below. When there are a plurality of separation membrane units 2A, 2B, and 2C as shown in this example, a gas may be supplied to the separation membrane units 2A, 2B, and 2C in sequence to perform scrubbing, or a predetermined amount of the gas is supplied to the whole separation membrane units 2A, 2B, and 2C, and at the same time, the supply amount of the gas may be increased in sequence to perform scrubbing.

It is preferable that the frequency of scrubbing to each of the separation membrane units 2A, 2B, and 2C (including frequency of increasing the supply amount of the gas for scrubbing) be made constant as much as possible from the viewpoint of maintaining performance stability of the whole separation membrane units 2A, 2B, and 2C. A gas supply time (including a time of increasing the supply amount of the gas) and an interval of scrubbing (including an interval to next increase the supply amount of the gas) are different depending on the operation condition. Therefore, an optimal condition needs to be determined by a small-scale experiment or from experiences. For example, when in a continuous fermentation apparatus including 10 separation membrane units, the scrubbing time (including a time of increasing the supply amount) for one separation membrane unit among the 10 separation membrane units is set to 1 minute and the separation membrane units are exchanged sequentially to perform scrubbing, and gas is supplied at a frequency of one in 10 minutes per unit to perform appropriate scrubbing washing.

The frequency of scrubbing for each of the separation membrane units 2A, 2B, and 2C (including the frequency of increasing the supply amount of the gas) is preferably 0.1 times/hour or more and 360 times/hour or less, and more preferably 12 times/hour or more and 120 times/hour or less. The frequency of scrubbing washing of 360 times/hour or less hardly causes problems such as damage to the separation membranes, and an increase in operation cost. Further, when the frequency of scrubbing washing is 0.1 times/hour or more, the washing effect can be sufficiently obtained.

The scrubbing washing time (including the time of increasing the supply amount of the gas) falls within a range of 5 seconds/time or more and 1 hour/time or less, and more preferably 10 seconds/time or more and 600 seconds/time or less. When the scrubbing washing time is within 1 hour, occurrence of problems such as damage and drying of the separation membranes and an increase in the operation cost is suppressed. Further, when the scrubbing washing time is 5 seconds or more, the washing effect can be sufficiently obtained.

The amount of the gas supplied to the separation membrane units 2A, 2B, and 2C can be measured with the flow meters 20A, 20B, and 20C. In the configuration of FIG. 1, the controller 22 can adjust the separation membrane units for scrubbing (or the gas supply amount) by detecting the gas supply amount measured with the flow meters 20A, 20B, and 20C, and switching opening and closing (or a degree of opening and closing) of the gas supply control valves 18A, 18B, and 18C.

The flow rate of the gas to the separation membrane units may be changed to two levels or to three or more levels by changing the opening degree of the valves. As described above, when a level at which the flow rate is 0 is included, a supply switch of ON/OFF may be provided.

An operation of performing scrubbing or sequentially switching to a separation membrane unit for which the supply amount of the gas is to be increased among the separation membrane units 2A, 2B, and 2C may be performed by controlling the opening and closing or the opening degree of the gas supply control valves 18A, 18B, and 18C on a pipe 28 that connects each of the separation membrane units 2A, 2B, and 2C to the scrubbing gas supply device 19 by the controller 22. The number of the separation membrane unit for which the supply amount of the gas is to be increased in a unit time among the separation membrane units 2A, 2B, and 2C may be one or two or more. At this time, the supply amount to the separation membrane units 2A, 2B, and 2C other than the above-described separation membrane units may be 0 or small as long as the kLa value falls within a certain range. A time of decreasing the supply amount of the gas to the whole separation membrane units 2A, 2B, and 2C and increasing the amount of the gas directly supplied to the fermentor 1 may be set.

More specifically, the controller 22 can control the flow rate of the gas supplied to the separation membrane unit 2A so that it is the largest of those of three separation membrane units (that is, a gas is supplied so that the supply amount of the gas to the separation membrane unit 2A is increased and the supply amount to other separation membrane units is made smaller than the former), then control the flow rate of the gas supplied to the separation membrane unit 2B so that it is the largest, and then control the flow rate of the gas supplied to the separation membrane unit 2C so that it is the largest. Thus, the controller 22 can sequentially switch to separation membrane units to which the largest flow rate of the gas is supplied.

The controller 22 may switch a separation membrane unit for which the supply amount of the gas is to be increased to another among a plurality of separation membrane units in a predetermined order (for example, to repeat the order of separation membrane units 2A, 2B, and 2C). Further, the controller 22 may control the flow rate of the gas so that the flow rate of a specific separation membrane unit is frequently larger than that of other separation membrane units.

The largest flow rate of the gas may be supplied to two or more separation membrane units at the same time. For example, in a configuration where five separation membrane units A, B, C, D, and E are arranged in parallel, the supply amounts of the gas to two separation membrane units among the five separation membrane units may be the same, and be larger than those of the other three.

3-5. Back Pressure Washing

The method of producing a chemical may further include a step of back pressure washing the separation membranes in the separation membrane units 2A, 2B, and 2C. In the configuration of FIG. 1, the pipes for washing 27A, 27B, and 27C connect to the downstream of the separation membrane units 2A, 2B, and 2C. Therefore, a washing solution can be charged in the separation membrane units 2A, 2B, and 2C by the washing pumps 16A, 16B, and 16C.

During back pressure washing, filtration is stopped so that the washing solution does not enter a filtrate tank for storing a filtrate. Specifically, the filtration valves 15A, 15B, and 15C are closed and the filtration pumps 14A, 14B, and 14C are stopped. In this state, when the washing valves 17A, 17B, and 17C are opened and the washing pumps 16A, 16B, and 16C are operated, back pressure washing is performed.

To stop back pressure washing, the washing valves 17A, 17B, and 17C are closed and the washing pumps 16A, 16B, and 16C are stopped. In this state, when the filtration valves 15A, 15B, and 15C are opened and the filtration pumps 14A, 14B, and 14C are operated, filtration is performed.

The controls can be performed by the controller 22. To determine initiation and termination times of back pressure washing, the continuous fermentation apparatus 100 may be equipped with a measuring device such as timer, which is not shown.

Examples of washing solution used in the back pressure washing may include a liquid that does not adversely affect fermentation and can wash the separation membranes such as water, a filtrate, a fermentation culture medium, a portion of components added to a fermentation culture medium, an aqueous solution of hydrochloric acid, sulfuric acid, sodium hydroxide, calcium hydroxide, or sodium hypochlorite, and a mixed liquid thereof.

4. kLa

A volumetric oxygen transfer coefficient kLa will be described. The volumetric oxygen transfer coefficient kLa (hereinafter simply abbreviated to kLa) exhibits an ability of transferring oxygen from a gas phase to a liquid phase in a unit time to produce dissolved oxygen during aerated and agitated culture, and can be represented by equation (1). The kLa is used in equation (2) that is an equation of balance of oxygen in a culture solution, represented by oxygen supplied from the gas phase and oxygen consumed by microorganisms during aerated and agitated culture (Seibutukogaku jikkensho, The Society for Biotechnology, Japan Ed, BAIFUKAN CO., LTD, p. 310 (1992)).

$$dC/dt = kLa \times (C^* - C) \tag{1}$$

In equation (1),

C: a concentration DO (ppm) of dissolved oxygen in a culture solution, $C^*$: a concentration DO (ppm) of dissolved oxygen equilibrated with a gas phase when oxygen is not consumed by microorganisms, and kLa: a volumetric oxygen transfer coefficient ($hr^{-1}$).

$$dC/dt = kLa \times (C^* - C) - QO2 \times X \tag{2}$$

In equation (2),

C: a concentration DO (ppm) of dissolved oxygen in a culture solution, $C^*$: a concentration DO (ppm) of dissolved oxygen equilibrated with a gas phase when oxygen is not consumed by microorganisms, X: a concentration (g/L) of cells, QO2: a specific respiration rate ($mgO_2/(g \; cell \cdot h)$), and kLa: a volumetric oxygen transfer coefficient ($hr^{-1}$).

A kLa in a culture reaction tank can be measured by a sulfite oxidation method (batch method-continuous method), a gas substitution method (gassing out method (a static method, a dynamic method)), an exhaust gas analysis, or the like (Seibutukogaku jikkensho, supra, p. 311). Hereinafter, one example of measurement of kLa by a gas substitution method (a dynamic method) will be shown.

Water or a culture medium to be used is first placed in a culture reaction tank, deoxygenation is caused by replacing oxygen in the liquid with nitrogen gas or adding sodium sulfite in an amount enough to reach a substantially saturated concentration, whereby the oxygen concentration in the liquid decreases. Subsequently, a dissolved oxygen concentration electrode is placed in the liquid, the aeration rate, the stirring rate, and the temperature are set to any conditions, and an increase process of dissolved oxygen is measured under the conditions. From equation (1) above, equation (3) is derived. Therefore, the kLa can be determined by plotting logarithms of ($C^*-C$) ppm relative to the aeration time.

$$Ln(C^*-C) = -kLa \times t \tag{3}$$

The kLa varies depending on various factors. These factors may include, for example, the amount of the culture solution, stirring of the culture solution in the fermentor 1, the aeration amount to the fermentor 1, and the temperature, in addition to the aeration amounts to the fermentor 1 and to the separation membrane units 2A, 2B, and 2C. The factors can be comparatively easily controlled during the continuous culture.

When the volumetric oxygen transfer coefficient kLa in the fermentor 1 is optimized to be kept constant and culture is performed, culturing in which high fermentation potency is maintained is made possible. For example, when the kLa is lower than the set value by 30% or more. In this case, the culture is much more anaerobic than an optimal culture condition, the sugar consumption rate decreases, the carbon source is excessively left, and the production rate of target chemical decreases. When the kLa is made constant, a chemical is obtained at high production rate, that is, extremely efficient production of a chemical is made possible. For example, as a method of producing lactic acid using recombinant yeast with a kLa fixed, JP 4806904 is exemplified.

A kLa in which a chemical production ability of cells to be cultured is maintained high is found by performing this measurement in advance, and the gas supply amount (V) in which the kLa can be maintained during supply of a gas to only one of the separation membrane units 2A, 2B, and 2C is measured. When the gas supply amount is divided into equal parts (V/3) and then supplied to the separation membrane units 2A, 2B, and 2C to obtain sufficient washing effect, supply of a gas can be dispersed into the separation membrane units 2A, 2B, and 2C or the fermentor 1, or the scrubbing time can be shortened. When the washing effect of the separation membrane units 2A, 2B, and 2C by the gas supply amount (V/3) is insufficient, the gas in a supply amount (V) capable of maintaining the kLa is sequentially supplied to the separation membrane modules 2A, 2B, and 2C, or the gas in a supply amount (V) capable of maintaining the kLa is divided into a gas for continuous supply ($V_1$) and a gas for intermittent supply ($V_2$), and the predetermined amount ($V_2$) of the gas is intermittently supplied to the separation membrane modules 2A, 2B, and 2C in order while the predetermined amount ($V_1/3$) of the gas is continuously supplied to the separation membrane modules 2A, 2B, and 2C. In this manner, the effect of scrubbing washing can be improved. When the washing effect is insufficient even by supply of at least two different amounts of the gas, the oxygen content in a gas to be passed can be decreased or the stirring rate in the fermentor 1 can be decreased, whereby the kLa can be set within a certain range.

5. Chemical

A chemical obtained by the production method described herein is a substance produced by cells in a culture solution. Examples of the chemical may include substances mass produced in the fermentation industry such as alcohols, organic acids, diamines, amino acids, and nucleic acids. The production method can also be applied to the production of a substance such as enzymes, antibiotics, and recombinant proteins.

Examples of the alcohols may include ethanol, 1,3-butanediol, 1,4-butanediol, and glycerol.

Examples of the organic acids may include acetic acid, lactic acid, pyruvic acid, succinic acid, malic acid, itaconic acid, amino acid, and citric acid. Examples of the diamines may include cadaverine. Examples of the nucleic acids may include inosine, guanosine, and cytidine.

Examples of the amino acids may include L-threonine, L-lysine, L-glutamic acid, L-tryptophan, L-isoleucine, L-glutamine, L-arginine, L-alanine, L-histidine, L-proline, L-phenylalanine, L-aspartic acid, L-tyrosine, L-methionine, L-serine, L-valine, and L-leucine. In particular, L-threonine, L-lysine, and L-glutamic acid are suitable.

EXAMPLES

Our apparatus and methods will be hereinafter described more specifically with reference to Examples. However, this disclosure is not limited to the Examples. A schematic configuration of a continuous fermentation apparatus used in the following Examples is the same as that shown in FIG. 1 except for the number of separation membrane units. In the following Examples, D-lactic acid and L-lysine were produced as a chemical by continuous fermentation.

A. Method of Measuring D-Lactic Acid Concentration

The concentration of D-lactic acid contained in a culture solution was measured using the following method. It was confirmed by weighing 100 μL of a culture solution containing D-lactic acid and measuring the amount of lactic acid under the following conditions by HPLC.

Column: Shim-Pack SPR-H (manufactured by SHIMADZU CORPORATION)

Mobile phase: 5 mM p-toluenesulfonic acid (flow rate: 0.8 mL/min)

Reaction liquid: 5 mM p-toluenesulfonic acid, 20 mM Bis-Tris, 0.1 mM EDTA 2Na (flow rate: 0.8 mL/min)

Detection method: electric conductivity

Temperature: 45° C.

A calibration curve was drawn by performing analysis using D-lactic acid having a known concentration as a standard sample and plotting the concentration of D-lactic acid on the horizontal axis and a detection peak area on the longitudinal axis.

B. Method of Measuring L-Lysine Concentration

The concentration of L-lysine contained in a culture solution was measured using the following method. 25 μL of a culture solution containing L-lysine to be measured was weighed, and to the solution, 400 μL of $NaHCO_3$ (75 mM) and 25 μL of 1,4-butanediol (2 g/L) as an internal standard were added. To the solution, 150 μL of 0.2 M dinitrofluorobenzene (DNFB) was added to cause a reaction at 37° C. for 1 hour.

50 μL of the solution was dissolved in 1 mL of acetonitrile and 10 μL of a supernatant obtained by centrifuging the solution at 10,000 rpm for 5 minutes was analyzed under the following conditions by HPLC.

Column: CAPCELLPAK C18 TYPE SG120 (manufactured by Shiseido Co., Ltd.)

Mobile phase: 0.1% (w/w) phosphoric acid aqueous solution:acetonitrile=45:55 (flow rate: 1 mL/min)

Detection method: UV (360 nm)

Temperature: 23° C.

A calibration curve was drawn by performing analysis using L-lysine having a known concentration as a standard sample and plotting the L-lysine concentration on the horizontal axis and a ratio of an L-lysine area/1,4-butanediol (internal standard) area on the longitudinal axis.

C. Method of Measuring Glucose Concentration and Concentration of Cells

"Glucose Test Wako C" (registered trademark) (available from Wako Pure Chemical Industries, Ltd.) was used for measurement of glucose concentration.

A concentration of cells was determined by measuring absorption of an appropriately diluted fermentation liquid at OD 600 nm.

D. Production of Membrane Filtration Module

A pressurized polyvinylidene fluoride hollow fiber membrane module "HFS 1020" manufactured by Toray Industries, Inc., was disassembled and only a portion not fixed with an adhesive was cut out. The polyvinylidene fluoride hollow fiber membrane thus cut out was housed in a case to produce a separation membrane module. As the case, a molded article made of a polycarbonate resin was used.

E. Production of Gene Recombinant Strain to be Used for Production of D-Lactic Acid by Continuous Fermentation As a microorganism having D-lactic acid production ability, yeast in which ldh genes derived from *Limulus polyphemus* were introduced into PDC1, SED1, and TDH3 loci was produced. Specifically, genetic modification was performed by a method described in WO2010/140602. The resulting strain was called SU042 strain. Using the SU042 strain, continuous fermentation of D-lactic acid was performed as described below.

For the strain, an optimal kLa exhibiting the highest D-lactic acid production ability was studied previously. The D-lactic acid production ability was found to be the highest at a kLa of 10.

F. Production of Gene Recombinant Strain to be Used for Production of L-Lysine by Continuous Fermentation As a microorganism having L-lysine production ability, a homoserine dehydrogenase (HOM) gene disrupted strain of *Corynebacterium glutamicum* ATCC13032 (hereinafter abbreviated as ATCC13032 strain) was produced. Specifically, genetic modification was performed by a method described in JP 2008-212138. The resulting strain is called *Corynebacterium glutamicum* delta-HOM strain (hereinafter abbreviated as delta-HOM strain). Using the delta-HOM strain, continuous fermentation of L-lysine was performed as described below.

For the strain, an optimal kLa exhibiting the highest L-lysine production ability was studied previously. The L-lysine production ability was found to be the highest at a kLa of 250.

G. Production of D-Lactic Acid by Continuous Fermentation

Comparative Example 1

Using the continuous fermentation apparatus 100 shown in FIG. 1, continuous fermentation of D-lactic acid was performed. For each separation membrane unit, one hollow fiber membrane module produced in [D] was used. Common operation conditions in continuous fermentation of D-lactic acid are as follows:

Common Conditions

Microorganism: *Saccharomyces cerevisiae* SU042 strain

Culture medium: fermentation culture medium (Table 1)

Volume of fermentation liquid: 1.0 (L)

Temperature: 32 (° C.)

Fermentor stirring rate: 400 (rpm)

Sterilization: a fermentor including a hollow fiber membrane module and a culture medium used were all subjected to high-pressure (2 air pressures) steam sterilization in an autoclave at 121° C. for 20 minutes.

pH Adjustment: adjusted to a pH of 4.5 with a 5 N calcium hydroxide suspension

Circulation pump flow rate: 1.7 L/min
Filtration rate of each separation membrane unit: 0.2 m³/m²/day (constant)
Number of separation membrane module per separation membrane unit: 1
Altered Conditions
Number of separation membrane unit: 4
Effective membrane area per unit: 70 cm²
Effective membrane area relative to all the units: 280 cm²
Conditions of gas supplied to each separation membrane unit from the scrubbing gas supply device 19: gas supply amount per unit: 100 mL/min, constantly supplied to all the units
Amount of gas supplied to fermentor 1 from fermentor gas supply device 21: 0 mL/min.
kLa under the gas supply conditions: 10

TABLE 1

| Yeast lactic acid fermentation medium | |
|---|---|
| Raw material sugar | 75 g |
| Ammonium sulfate | 1.5 g |
| | Up to 1L |

A SU042 strain scraped off from an agar culture medium was inoculated in a test tube charged with 5 mL of SC culture medium (100 g/L of glucose, 6.7 g/L of yeast nitrogen base, 152 mg/L of 19 standard amino acids other than leucine, 760 mg/L of leucine, 152 mg/L of inositol, 16 mg/L of p-aminobenzoic acid, 40 mg/mL of adenine, and 152 mg/L of uracil). This strain was subjected to shake the culture at 30° C. for 24 hours (pre-preculture). The whole amount of the pre-preculture solution obtained was inoculated in a 500-mL erlenmeyer flask charged with 50 mL of culture medium shown in Table 1 and precultured at 30° C. The preculture solution obtained was inoculated in a continuous fermentation apparatus charged with 1.0 L of D-lactic acid fermentation culture medium and cultured for 24 hours. Subsequently, the D-lactic acid fermentation culture medium was continuously supplied while the supply amount of the culture solution was controlled to make the amount of the culture solution in the fermentor constant. Thus, continuous culture was performed to produce D-lactic acid by continuous fermentation.

The concentration of D-lactic acid produced in the filtrate and the residual glucose concentration were appropriately measured by the methods shown in [A] and [C].

Figure 3:
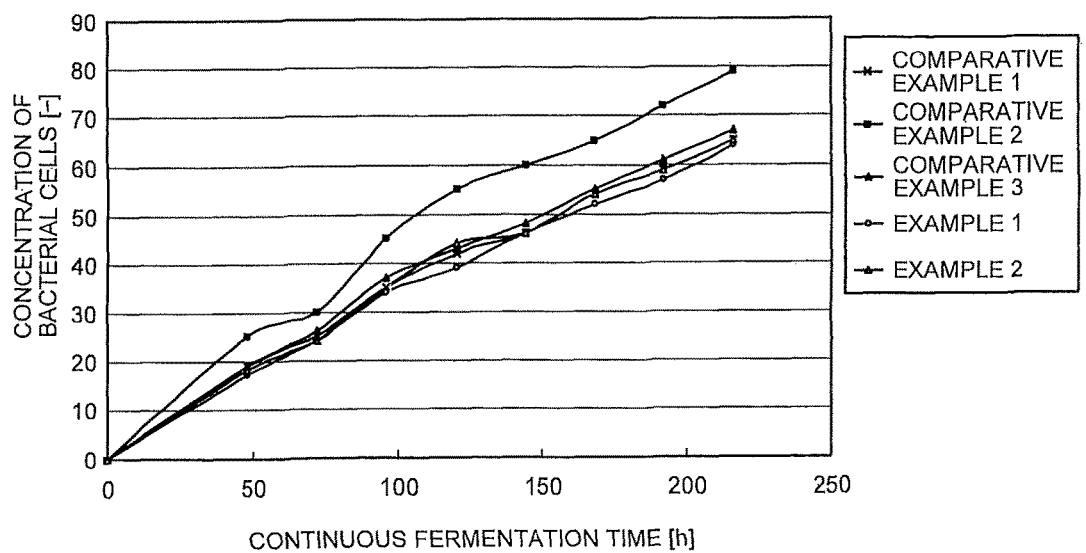
FIG. 3 is a graph showing a change in the concentration of cells in Comparative Examples 1 to 3 and Examples 1 and 2.
Figure 4:
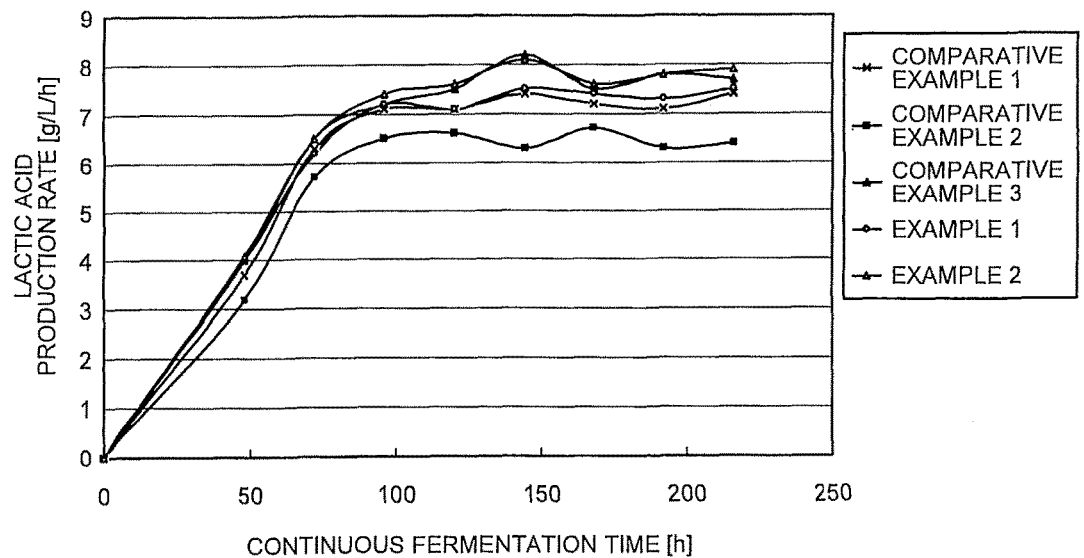
FIG. 4 is a graph showing a change in the production rate in Comparative Examples 1 to 3 and Examples 1 and 2.
Figure 5:
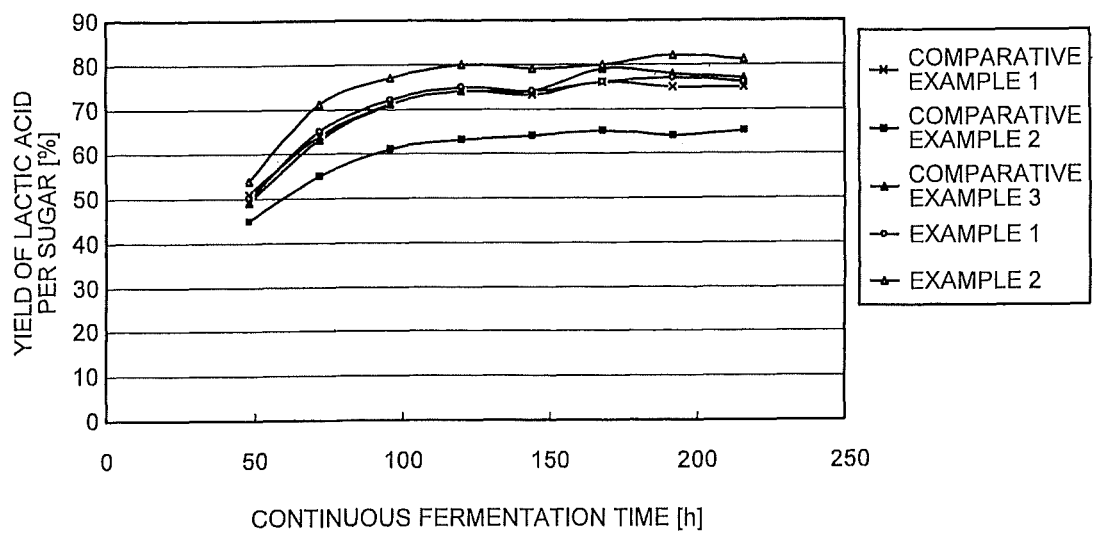
FIG. 5 is a graph showing a change in the yield per sugar in Comparative Examples 1 to 3 and Examples 1 and 2.
Figure 6:
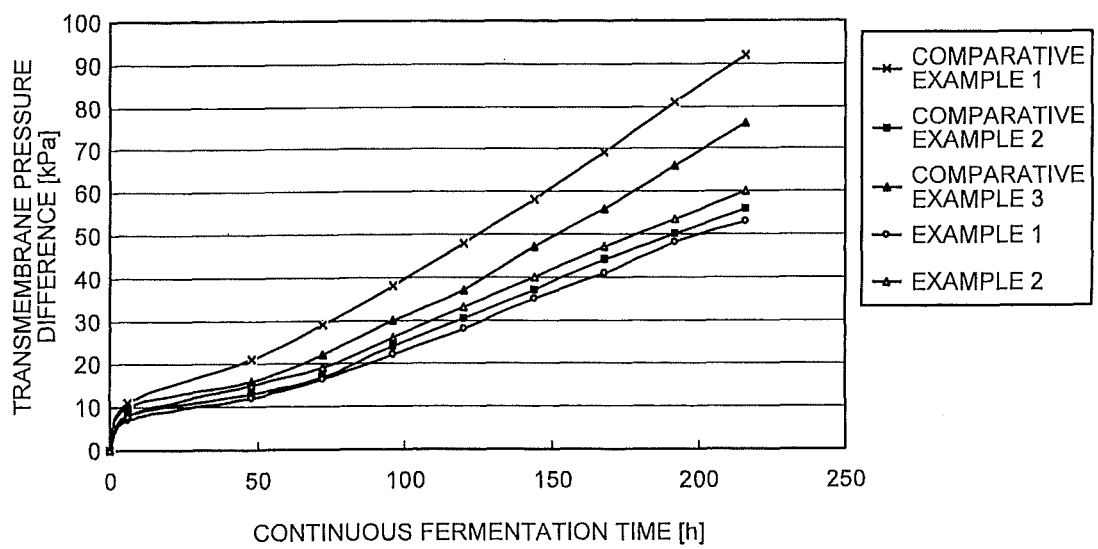
FIG. 6 is a graph showing a change in the transmembrane pressure difference in Comparative Examples 1 to 3 and Examples 1 and 2.

Changes in the concentration (−) of cells in the fermentation liquid in this Comparative Example are shown in FIG. 3, changes in the D-lactic acid production rate (g/L/h) are shown in FIG. 4, and changes in the yield (%) per sugar are shown in FIG. 5. In addition, changes in the transmembrane pressure difference (kPa) are shown in FIG. 6.

Comparative Example 2

Continuous fermentation was performed under the same conditions as in Comparative Example 1 except for the following conditions:
Altered Conditions
Number of separation membrane unit: 4
Effective membrane area per unit: 70 cm²
Effective membrane area relative to all the units: 280 cm²
Conditions of gas supplied to each separation membrane unit from the scrubbing gas supply device 19: gas supply amount per unit: 400 mL/min, constantly supplied to all the units
Amount of gas supplied to fermentor 1 from fermentor gas supply device 21: 0 mL/min.
kLa under the gas supply conditions: 50
Changes in the concentration (−) of cells in the fermentation liquid in this Comparative Example are shown in FIG. 3, changes in the D-lactic acid production rate (g/L/h) are shown in FIG. 4, and changes in the yield (%) per sugar are shown in FIG. 5. In addition, changes in the transmembrane pressure difference (kPa) are shown in FIG. 6.

Comparative Example 3

Continuous fermentation was performed under the same conditions as in Comparative Example 1 except for the following conditions:
Altered Conditions
Number of separation membrane unit: 1
Effective membrane area per unit: 280 cm²
Effective membrane area relative to all the units: 280 cm²
Conditions of gas supplied to separation membrane units from the scrubbing gas supply device 19: gas supply amount per unit: 400 mL/min, constantly supplied
Amount of gas supplied to fermentor 1 from fermentor gas supply device 21: 0 mL/min.
kLa under the gas supply conditions: 7
Changes in the concentration (−) of cells in the fermentation liquid in this Comparative Example are shown in FIG. 3, changes in the D-lactic acid production rate (g/L/h) are shown in FIG. 4, and changes in the yield (%) per sugar are shown in FIG. 5. In addition, changes in the transmembrane pressure difference (kPa) are shown in FIG. 6.

Example 1

Continuous fermentation was performed under the same conditions as in Comparative Example 1 except for the following conditions:
Altered Conditions
Number of separation membrane unit: 4
Effective membrane area per unit: 70 cm²
Effective membrane area relative to all the units: 280 cm²
Conditions of gas supplied to each separation membrane unit from the scrubbing gas supply device 19: repeating supply of a gas to each unit at 400 mL/min for 2.5 minutes and no supply of a gas (0 mL/min) for 7.5 minutes, and controlling supply of a gas for 2.5 minutes, during which the supply amount of the gas is increased so that the gas is not supplied simultaneously to the units
Amount of gas supplied to fermentor 1 from fermentor gas supply device 21: 0 mL/min.
kLa under the gas supply conditions: 10
Changes in the concentration (−) of cells in the fermentation liquid in this Example are shown in FIG. 3, changes in the D-lactic acid production rate (g/L/h) are shown in FIG. 4, and changes in the yield (%) per sugar are shown in FIG. 5. In addition, changes in the transmembrane pressure difference (kPa) are shown in FIG. 6.

The yield per sugar and the D-lactic acid production rate are the same as those in Comparative Example 1, while the increasing rate of transmembrane pressure difference changes in low levels. It is confirmed that high membrane washing effect is obtained while the same fermentation efficiency is ensured. Although the increasing rate of transmembrane pressure difference is the same as in Comparative Example 2, higher yield per sugar and D-lactic acid production rate are exhibited. Therefore, improvement of fermentation efficiency is confirmed. The yield per sugar and the D-lactic acid production rate are the same as in Comparative Example 3, while the increasing rate of transmembrane pressure difference changes in slightly low levels. The membrane area and the aeration amount are the same as in Comparative Example 3, but a plurality of MD are used. Thus, it is confirmed that high membrane washing effect is obtained while the same fermentation efficiency is ensured.

Example 2

Continuous fermentation was performed under the same conditions as in Comparative Example 1 except for the following conditions:
Altered Conditions
  Number of separation membrane unit: 4
  Effective membrane area per unit: 70 cm$^2$
  Effective membrane area relative to all the units: 280 cm$^2$
  Conditions of gas supplied to each separation membrane unit from the scrubbing gas supply device 19: repeating supply of a gas to each unit at 300 mL/min for 2.5 minutes and supply of a gas at 10 mL/min for 7.5 minutes, and controlling supply of a gas for 2.5 minutes, during which the supply amount of the gas is increased so that the gas is not supplied simultaneously to the units
  Amount of gas supplied to fermentor 1 from fermentor gas supply device 21: 100 mL/min.
  kLa under the gas supply conditions: 10

Changes in the concentration (−) of cells in the fermentation liquid in this Example are shown in FIG. 3, changes in the D-lactic acid production rate (g/L/h) are shown in FIG. 4, and changes in the yield (%) per sugar are shown in FIG. 5. In addition, changes in the transmembrane pressure difference (kPa) are shown in FIG. 6.

The yield per sugar and the D-lactic acid production rate are the same as those in Comparative Example 1, while the increasing rate of transmembrane pressure difference changes in low levels. It is confirmed that high membrane washing effect is obtained while the same fermentation efficiency is ensured. Although the increasing rate of transmembrane pressure difference is the same as in Comparative Example 2, higher yield per sugar and D-lactic acid production rate are exhibited. Therefore, improvement of fermentation efficiency is confirmed.

I. Production of L-Lysine by Continuous Fermentation

Comparative Example 4

Using the continuous fermentation apparatus 100 shown in FIG. 1, continuous fermentation of L-lysine was performed. For each separation membrane unit, a hollow fiber membrane module produced in [D] was used. Operation conditions in continuous fermentation of L-lysine common to those in the following Examples and Comparative Examples are as follows:
Common Conditions
  Microorganism: *Corynebacterium glutamicum* delta-HOM strain
  Culture medium: lysine fermentation culture medium (Table 2)
  Volume of fermentation liquid: 3.0 (L)
  Temperature: 30 (° C.)
  Fermentor stirring rate: 350 (rpm)
  Sterilization: a fermentor including a hollow fiber membrane module and a culture medium used were all subjected to high-pressure (2 air pressures) steam sterilization in an autoclave at 121° C. for 20 minutes.
  pH Adjustment: adjusted to a pH of 7.3 with a 28% aqueous ammonia solution.
  Circulating pump flow rate: 3.0 L/min
  Filtration rate of each separation membrane unit: 0.2 m$^3$/m$^2$/day (constant)
  Number of separation membrane module per separation membrane unit: 1
Altered Conditions
  Number of separation membrane unit: 4
  Effective membrane area per unit: 70 cm$^2$
  Effective membrane area relative to all the units: 280 cm$^2$
  Conditions of gas supplied to each separation membrane unit from the scrubbing gas supply device 19: gas supply amount per unit: 280 mL/min, constantly supplied to all the units
  Amount of gas supplied to fermentor 1 from fermentor gas supply device 21: 0 mL/min.
  kLa under the gas supply conditions: 200

TABLE 2

| L-lysine fermentation medium for corynebacterium | | |
|---|---|---|
| Component | Amount | Unit |
| Glucose | 100 | g/L |
| Urea | 1 | g/L |
| Yeast extract | 5 | g/L |
| Dipotassium hydrogen phosphate | 2.5 | g/L |
| Magnesium sulfate heptahydrate | 175 | g/L |
| Calcium chloride dihydrate | 205 | g/L |
| Iron sulfate heptahydrate | 0.05 | g/L |
| Manganese sulfate pentahydrate | 13 | ppm |
| Copper sulfate pentahydrate | 6.3 | ppm |
| Zinc sulfate heptahydrate | 13 | ppm |
| Nickel chloride hexahydrate | 5 | ppm |
| Cobalt chloride hexahydrate | 1.3 | ppm |
| Molybdenum | 1.3 | ppm |
| β-alanine | 23 | ppm |
| Nicotinic acid | 14 | ppm |
| Biotin | 0.5 | ppm |
| Thiamine | 7 | ppm |

A delta-HOM strain scraped off from an agar culture medium was inoculated in a test tube charged with 5 mL of BY culture medium (0.5% yeast extract, 0.7% meat extract, 1% peptone, and 0.3% sodium chloride). This strain was subjected to shake culture at 30° C. for 24 hours (pre-preculture). The whole amount of the pre-preculture solution obtained was inoculated in a 500-mL erlenmeyer flask charged with 50 mL of culture medium shown in Table 2 and precultured at 30° C. The preculture solution obtained was inoculated in a continuous fermentation apparatus charged with 3 L of L-lysine fermentation culture medium and cultured for 24 hours. Subsequently, an L-lysine fermentation culture medium was continuously supplied while the supply amount of the culture solution was controlled to make the amount of the culture solution in the fermentor constant. Thus, continuous fermentation was performed to produce L-lysine by continuous fermentation.

The concentration of L-lysine produced in the filtrate and the residual glucose concentration were appropriately measured using the methods shown in [B] and [C].

Figure 7:
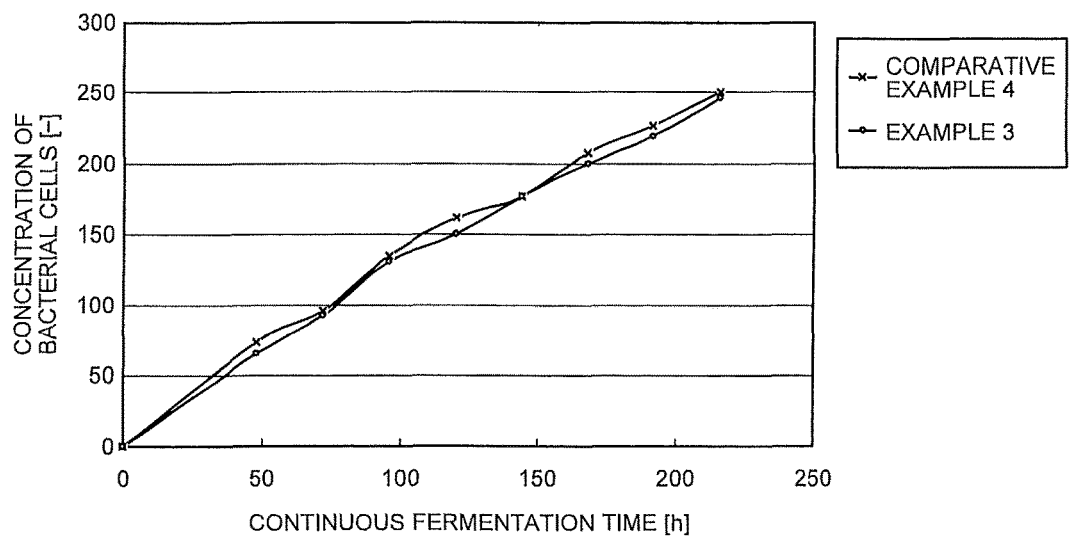
FIG. 7 is a graph showing a change in the concentration of cells in Comparative Example 4 and Example 3.
Figure 8:
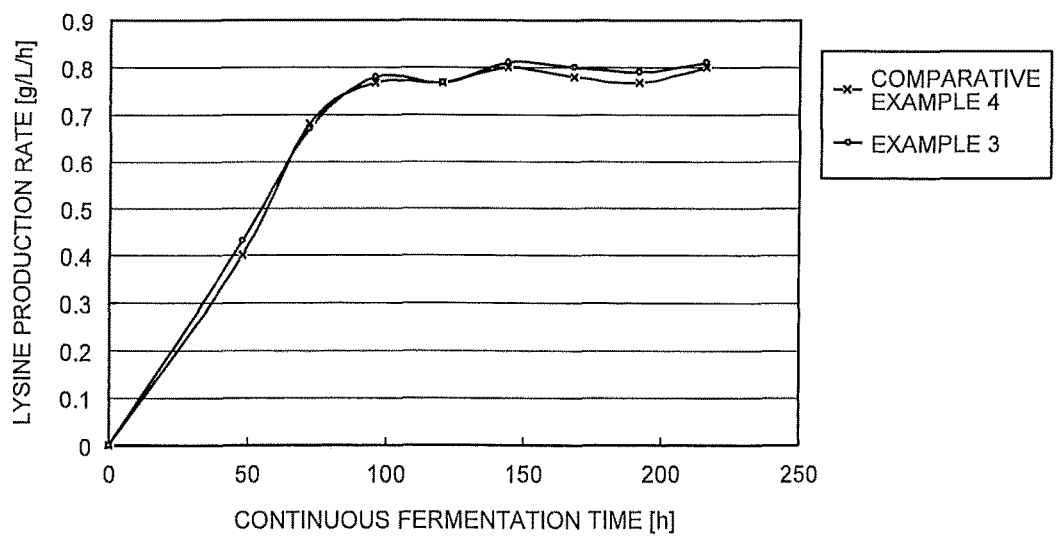
FIG. 8 is a graph showing a change in the production rate in Comparative Example 4 and Example 3.
Figure 9:
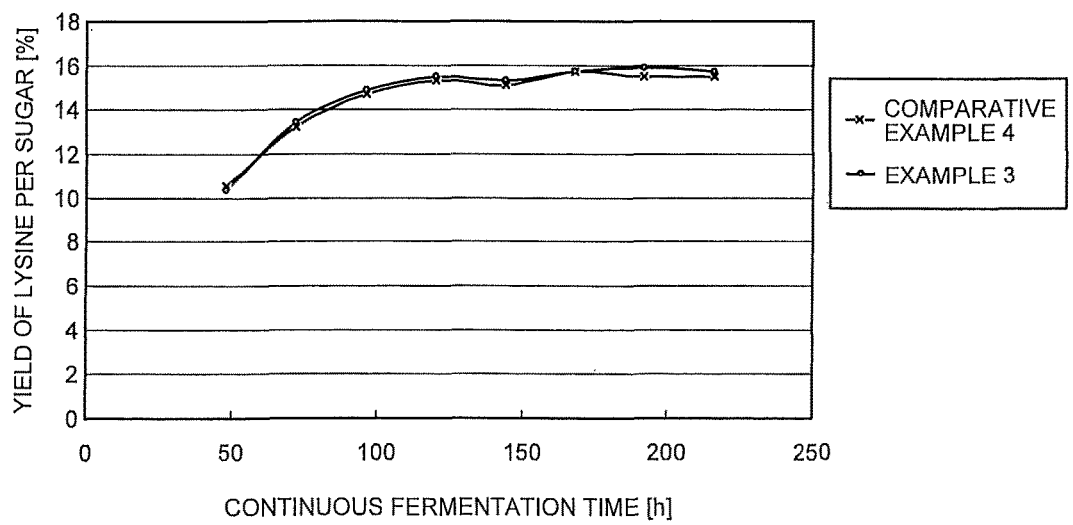
FIG. 9 is a graph showing a change in the yield per sugar in Comparative Example 4 and Example 3.
Figure 10:
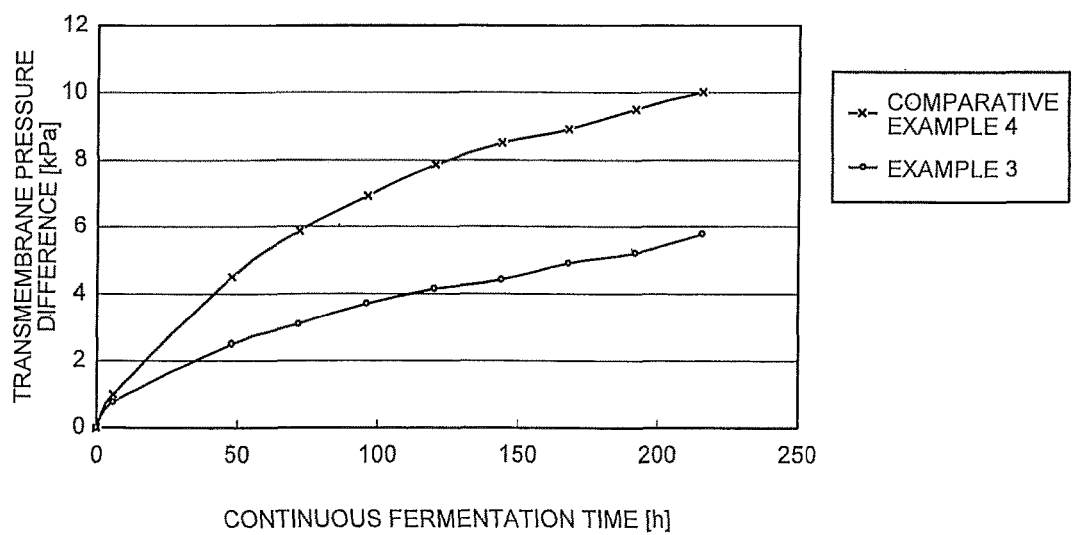
FIG. 10 is a graph showing a change in the transmembrane pressure difference in Comparative Example 4 and Example 3.

Changes in the concentration (−) of cells in the fermentation liquid in this Comparative Example are shown in FIG. 7, changes in the L-lysine production rate (g/L/h) are shown in FIG. 8, and changes in the yield (%) per sugar are shown in FIG. 9. In addition, changes in the transmembrane pressure difference (kPa) are shown in FIG. 10.

Example 3

Continuous fermentation was performed under the same conditions as those in Comparative Example 5 except for the following conditions:
Altered Conditions
Number of separation membrane unit: 4
Effective membrane area per unit: 70 cm$^2$
Effective membrane area relative to all the units: 280 cm$^2$
Conditions of gas supplied to each separation membrane unit from the scrubbing gas supply device 19: repeating supply of a gas to each unit at 900 mL/min for 2.5 minutes and supply of a gas at 10 mL/min for 7.5 minutes, and controlling supply of a gas for 2.5 minutes, during which the supply amount of the gas is increased so that the gas is not supplied simultaneously to the units
Amount of gas supplied to fermentor 1 from fermentor gas supply device 21: 0 mL/min.
kLa under the gas supply conditions: 200
Changes in the concentration (–) of cells in the fermentation liquid in this Example are shown in FIG. 7, changes in the L-lysine production rate (g/L/h) are shown in FIG. 8, and changes in the yield (%) per sugar are shown in FIG. 9. In addition, changes in the transmembrane pressure difference (kPa) are shown in FIG. 10.

The yield per sugar and the L-lysine production rate are the same as those in Comparative Example 4, while the increasing rate of transmembrane pressure difference is suppressed and changes in low levels. Therefore, it is confirmed that the same L-lysine production efficiency and high membrane washing effect are obtained.

INDUSTRIAL APPLICABILITY

In a continuous fermentation apparatus including a fermentor, a plurality of separation membrane units, and a circulation system, there is provided a simple method in which the supply amount of a gas containing oxygen to be supplied to the apparatus is set on the basis of an optimal kLa value for cells to be cultured in the continuous fermentation apparatus, and different amounts of the gas are sequentially supplied to the plurality of separation membrane units so that the kLa value is within a constant range from the optimal kLa value. Since the long-term stability of separation membrane unit operation and the fermentation result can be improved, a chemical that is a fermentation product and is widely used in the fermentation industry can be stably produced at low cost by the simple method.

The invention claimed is:

1. A method of producing a chemical comprising:
a chemical production step of culturing cells in a culture solution in a fermentor to ferment a feedstock to produce a chemical;
a culture solution supply step of supplying the culture solution containing the chemical produced in the chemical production step to a plurality of separation membrane units arranged in parallel;
a filtration step of filtering the culture solution supplied in the culture solution supply step to separate a permeate containing the chemical;
a reflux step of refluxing a retentate not filtered in the filtration step to the fermentor; and
a washing step of washing the plurality of separation membrane units by scrubbing with a gas containing oxygen and having at least two different flow rates for the plurality of separation membrane units while supplying the culture solution to the plurality of separation membrane units, wherein
the supply amount and supply time of the gas containing oxygen supplied in the chemical production step and the washing step are set so that a kLa value is within a predetermined range from an optimal kLa value for the cells cultured in the chemical production step.

2. The method according to claim 1, wherein, in the washing step, a flow rate of the gas supplied to the plurality of separation membrane units is changed to two or more levels and the separation membrane units are sequentially switched for supply of a largest flow rate of the gas.

3. The method according to claim 2, wherein, in the filtration step, a filtration operation is intermittently performed.

4. The method according to claim 2, wherein the cells are bacteria.

5. The method according to claim 2, wherein the cells are yeast.

6. The method according to claim 2, wherein the chemical is an amino acid.

7. The method according to claim 2, wherein the chemical is an organic acid.

8. The method according to claim 1, wherein the cells are bacteria.

9. The method according to claim 8, wherein the bacteria are bacteria belonging to any of a genus *Escherichia*, a genus *Providencia*, a genus *Corynebacterium*, a genus *Brevibacterium*, and a genus *Serratia*.

10. The method according to claim 8, wherein the bacteria are any of *Escherichia coli, Providencia rettgeri, Corynebacterium glutamicum, Brevibacterium flavum, Brevibacterium lactofermentum*, and *Serratia marcescens*.

11. The method according to claim 1, wherein the cells are yeast.

12. The method according to claim 1, wherein the chemical is an amino acid.

13. The method according to claim 12, wherein the amino acid is L-threonine, L-lysine, L-glutamic acid, L-tryptophan, L-isoleucine, L-glutamine, L-arginine, L-alanine, L-histidine, L-proline, L-phenylalanine, L-aspartic acid, L-tyrosine, L-methionine, L-serine, L-valine, or L-leucine.

14. The method according to claim 1, wherein the chemical is an organic acid.

15. The method according to claim 14, wherein the chemical is lactic acid.

16. The method according to claim 1, wherein the chemical is cadaverine.

* * * * *